(12) United States Patent
Peyser et al.

(10) Patent No.: US 10,881,339 B2
(45) Date of Patent: Jan. 5, 2021

(54) USE OF SENSOR REDUNDANCY TO DETECT SENSOR FAILURES

(71) Applicant: DexCom, Inc., San Diego, CA (US)

(72) Inventors: Thomas A. Peyser, Menlo Park, CA (US); Naresh C. Bhavaraju, San Diego, CA (US); Leif N. Bowman, Livermore, CA (US); Apurv Ullas Kamath, San Diego, CA (US); Aarthi Mahalingam, San Diego, CA (US); Jack Pryor, San Diego, CA (US); Peter C. Simpson, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 738 days.

(21) Appl. No.: 13/789,279

(22) Filed: Mar. 7, 2013

(65) Prior Publication Data
US 2014/0005505 A1    Jan. 2, 2014

Related U.S. Application Data

(60) Provisional application No. 61/666,625, filed on Jun. 29, 2012, provisional application No. 61/666,622, (Continued)

(51) Int. Cl.
*A61B 5/145* (2006.01)
*A61B 5/1495* (2006.01)
(Continued)

(52) U.S. Cl.
CPC .......... *A61B 5/1495* (2013.01); *A61B 5/1459* (2013.01); *A61B 5/1473* (2013.01);
(Continued)

(58) Field of Classification Search
CPC .................................................. A61B 5/14532
(Continued)

(56) References Cited

U.S. PATENT DOCUMENTS 6,558,351 B1   5/2003   Steil et al.
6,560,471 B1   5/2003   Heller et al.
(Continued)

FOREIGN PATENT DOCUMENTS

WO   WO 2012/174563   12/2012

OTHER PUBLICATIONS

Klueh et al., Metabolic Biofouling of Glucose Sensors in Vivo: Role of Tissue Microhemorrhages. J Diabetes Science Technol. (2011) 5(3):583-595.
(Continued)

*Primary Examiner* — Puya Agahi
(74) *Attorney, Agent, or Firm* — Knobbe, Martens, Olson & Bear, LLP

(57) ABSTRACT

Devices, systems, and methods for providing more accurate and reliable sensor data and for detecting sensor failures. Two or more electrodes can be used to generate data, and the data can be subsequently compared by a processing module. Alternatively, one sensor can be used, and the data processed by two parallel algorithms to provide redundancy. Sensor performance, including sensor failures, can be identified. The user or system can then respond appropriately to the information related to sensor performance or failure.

20 Claims, 9 Drawing Sheets

Related U.S. Application Data filed on Jun. 29, 2012, provisional application No. 61/666,618, filed on Jun. 29, 2012.

(51) Int. Cl.
*A61B 5/1473* (2006.01)
*A61B 5/1459* (2006.01)
*A61B 5/00* (2006.01)
*A61B 5/1486* (2006.01)

(52) U.S. Cl.
CPC ...... *A61B 5/14532* (2013.01); *A61B 5/14865* (2013.01); *A61B 5/7221* (2013.01); *A61B 5/7246* (2013.01); *A61B 5/7278* (2013.01); *A61B 2562/04* (2013.01)

(58) Field of Classification Search
USPC .................................................. 600/347, 365
See application file for complete search history.

(56) References Cited

U.S. PATENT DOCUMENTS

| | | | |
|---|---|---|---|
| 6,666,821 B2 | 12/2003 | Keimel | |
| 6,770,030 B1 | 8/2004 | Schaupp et al. | |
| 6,809,653 B1 | 10/2004 | Mann et al. | |
| 6,918,874 B1 | 7/2005 | Hatch et al. | |
| 8,116,840 B2 | 2/2012 | Feldman et al. | |
| 9,974,472 B2 | 5/2018 | Hayter et al. | |
| 10,598,627 B2 | 3/2020 | Bhavaraju et al. | |
| 2005/0056552 A1* | 3/2005 | Simpson | A61B 5/14532 205/782 |
| 2005/0143635 A1* | 6/2005 | Kamath | A61B 5/14532 600/347 |
| 2006/0195029 A1* | 8/2006 | Shults | A61B 5/0002 600/345 |
| 2007/0027370 A1 | 2/2007 | Brauker et al. | |
| 2007/0208246 A1* | 9/2007 | Brauker | A61B 5/746 600/365 |
| 2007/0235331 A1 | 10/2007 | Simpson et al. | |
| 2007/0299617 A1 | 12/2007 | Willis | |
| 2008/0000079 A1 | 1/2008 | Gabriel et al. | |
| 2008/0000779 A1 | 1/2008 | Wang et al. | |
| 2008/0027287 A1 | 1/2008 | Shah et al. | |
| 2008/0076974 A1 | 3/2008 | Yamazaki et al. | |
| 2008/0161664 A1* | 7/2008 | Mastrototaro | A61B 5/14532 600/347 |
| 2008/0249385 A1 | 10/2008 | Phan et al. | |
| 2008/0287762 A1 | 11/2008 | Hayter et al. | |
| 2008/0300572 A1* | 12/2008 | Rankers | A61B 5/14532 604/504 |
| 2009/0018424 A1 | 1/2009 | Kamath et al. | |
| 2009/0023222 A1 | 1/2009 | Wu et al. | |
| 2009/0030641 A1 | 1/2009 | Fjield et al. | |
| 2009/0043288 A1 | 2/2009 | Petrakis | |
| 2009/0082693 A1 | 3/2009 | Stafford | |
| 2009/0105605 A1 | 4/2009 | Abreu et al. | |
| 2009/0120810 A1* | 5/2009 | Phan | A61B 5/14532 205/792 |
| 2009/0131769 A1 | 5/2009 | Leach et al. | |
| 2009/0275815 A1 | 11/2009 | Bickoff et al. | |
| 2010/0087900 A1* | 4/2010 | Flint | A61B 5/1101 607/104 |
| 2010/0185071 A1* | 7/2010 | Simpson | A61B 5/14532 600/347 |
| 2010/0219085 A1 | 9/2010 | Oviatt et al. | |
| 2010/0230285 A1 | 9/2010 | Hoss et al. | |
| 2010/0268304 A1* | 10/2010 | Matos | G16H 40/63 607/60 |
| 2010/0292557 A1 | 11/2010 | Pesach et al. | |
| 2010/0319436 A1* | 12/2010 | Sun | A61B 5/01 73/61.46 |
| 2011/0021932 A1 | 1/2011 | Kim et al. | |
| 2011/0024307 A1* | 2/2011 | Simpson | A61B 5/14532 205/782 |
| 2011/0027127 A1 | 2/2011 | Simpson et al. | |
| 2011/0218489 A1 | 9/2011 | Mastrototaro et al. | |
| 2011/0224516 A1* | 9/2011 | Romey | A61B 5/14532 600/317 |
| 2011/0237916 A1 | 9/2011 | Hanson et al. | |
| 2012/0028283 A1 | 2/2012 | Hoss et al. | |
| 2012/0078071 A1 | 3/2012 | Böhm et al. | |
| 2012/0097554 A1* | 4/2012 | Shah | A61B 5/1473 205/782 |
| 2012/0262298 A1 | 10/2012 | Böhm et al. | |
| 2012/0265035 A1 | 10/2012 | Böhm et al. | |
| 2013/0060105 A1 | 3/2013 | Shah et al. | |
| 2013/0112573 A1 | 5/2013 | Noble et al. | |
| 2013/0331673 A1 | 12/2013 | Gautham et al. | |
| 2014/0005508 A1 | 1/2014 | Estes et al. | |
| 2014/0005509 A1 | 1/2014 | Bhavaraju et al. | |
| 2015/0090589 A1 | 4/2015 | Estes et al. | |

OTHER PUBLICATIONS

International Preliminary Report on Patentability for Application No. PCT/US2013/047527 dated Jan. 8, 2015, 12 pages.
International Preliminary Report on Patentability for Application No. PCT/US2013/047537 dated Jan. 8, 2015, 8 pages.
International Preliminary Report on Patentability for Application No. PCT/US2013/047543 dated Jan. 8, 2015, 12 pages.
International Search Report and Written Opinion for Application No. PCT/US2013/047527 dated Nov. 15, 2013, 17 pages.
International Search Report and Written Opinion for Application No. PCT/US2013/047537 dated Sep. 9, 2013, 11 pages.
International Search Report and Written Opinion for Application No. PCT/US2013/047543 dated Nov. 15, 2013, 16 pages.

* cited by examiner

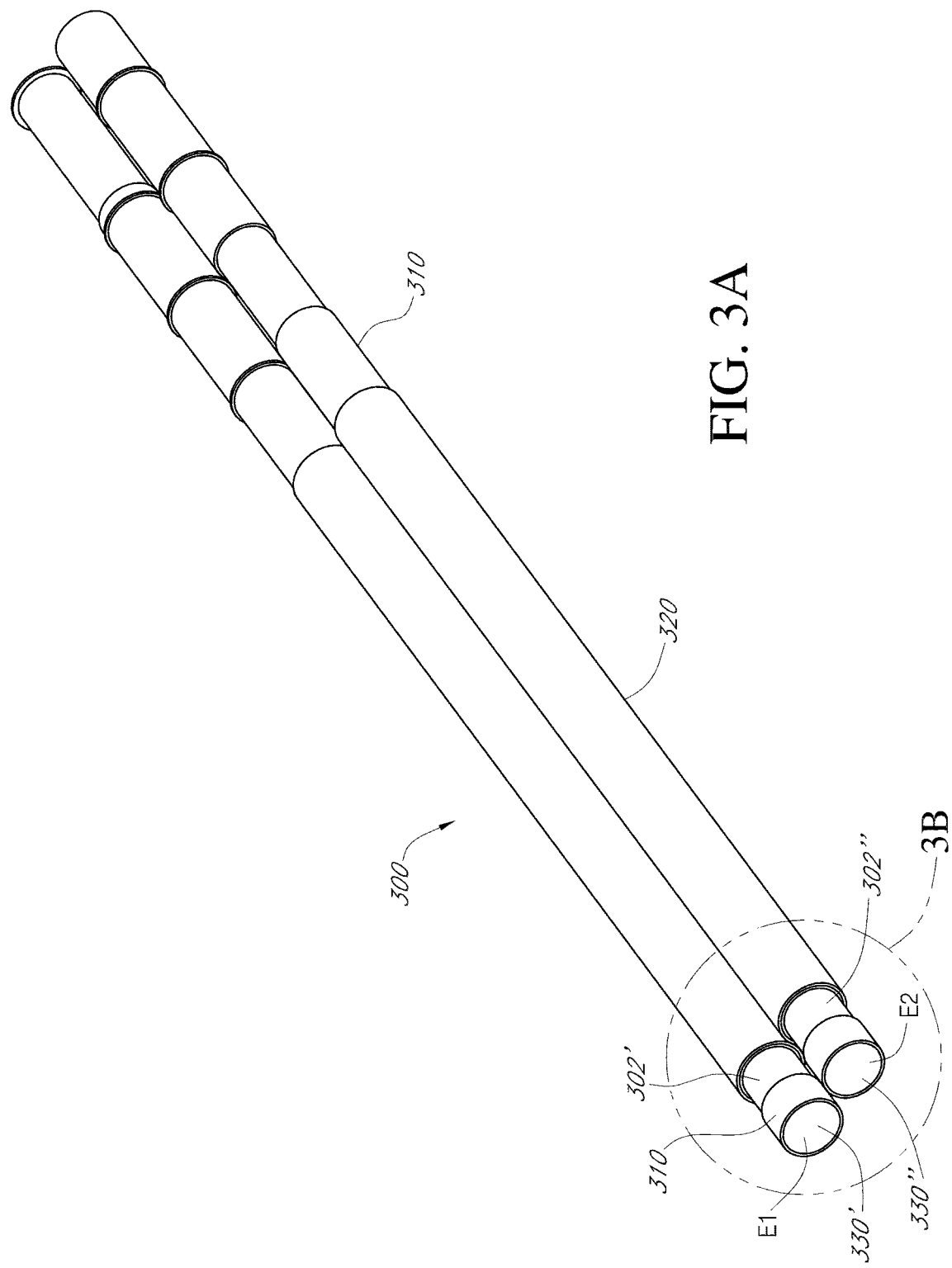

USE OF SENSOR REDUNDANCY TO DETECT SENSOR FAILURES

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 61/666,625, filed Jun. 29, 2012, U.S. Provisional Application No. 61/666,622, filed Jun. 29, 2012, and U.S. Provisional Application No. 61/666,618, filed Jun. 29, 2012, the disclosures of which are hereby expressly incorporated by reference in their entirety and are hereby expressly made a portion of this application.

FIELD OF THE INVENTION

The embodiments described herein relate generally to devices, systems, and methods for processing sensor data and for responding to changes in sensor function.

BACKGROUND OF THE INVENTION

Diabetes mellitus is a chronic disease, which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (such as, for example, kidney failure, skin ulcers, or bleeding into the vitreous of the eye) associated with the deterioration of small blood vessels. Sometimes, a hypoglycemic reaction (low blood sugar) is induced by an inadvertent overdose of insulin, or after a normal dose of insulin or glucose-lowering agent accompanied by extraordinary exercise or insufficient food intake.

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood glucose values. Many conventional implantable glucose sensors suffer from complications within the body and provide only short-term or less-than-accurate sensing of blood glucose. Additionally, many conventional transcutaneous sensors have problems in accurately sensing and reporting back glucose or analyte values continuously over extended periods of time due to non-analyte-related signals caused by interfering species or unknown noise-causing events. Thus, there is a need for more reliable devices, systems, and methods for continuously sensing and reporting back glucose or analyte values.

SUMMARY OF THE INVENTION

There is a need for more reliable devices, systems, and methods for continuously sensing and reporting back glucose or analyte values.

Accordingly, in a first aspect a method is provided for detecting a sensor failure in a continuous analyte monitoring system implanted in a host, the method comprising: receiving first sensor data from a first electrode implanted in the host, wherein the first sensor data are indicative of a property corresponding to the first electrode; receiving second sensor data from a second electrode implanted in the host, wherein the second sensor data are indicative of the property corresponding to the second electrode, the first electrode and the second electrode having substantially same characteristics; comparing, using a processor module, the property corresponding to the first electrode with the property corresponding to the second electrode; and identifying a failure in at least one of the first electrode or the second electrode when a property magnitude of the first electrode is different from a property magnitude of the second electrode by a predetermined value.

In an embodiment of the first aspect, the property is sensor sensitivity to an analyte.

In an embodiment of the first aspect, the property is baseline.

In an embodiment of the first aspect, the first electrode is located substantially adjacent to the second electrode.

In an embodiment of the first aspect, the first electrode and the second electrode are separated by a distance of less than about 1 mm at a closest proximity.

In an embodiment of the first aspect, the first electrode and the second electrode are separated by a distance of less than about 0.5 mm at a closest proximity.

In a second aspect, a method is provided for detecting a sensor failure in a continuous analyte monitoring system implanted in a host, the method comprising: receiving first sensor data over a time period from a first electrode implanted in the host, wherein the first sensor data are indicative of a property corresponding to the first electrode; receiving second sensor data over the time period from a second electrode implanted in the host, wherein the second sensor data are indicative of the property corresponding to the second electrode, the first and second electrodes having substantially same characteristics; determining, using a processor module, over the time period a correlation between the property corresponding to the first electrode with the property corresponding to the second electrode; and identifying a failure in at least one of the first electrode or the second electrode when the correlation is less than a predetermined value.

In a third aspect, a method is provided detecting a sensor failure in a continuous analyte monitoring system implanted in a host, the method comprising: receiving first sensor data over a time period from a first electrode implanted in the host, wherein the first sensor data are indicative of a first property and a second property corresponding to the first electrode; receiving second sensor data over the time period from a second electrode implanted in the host, wherein the second sensor data are indicative of the first property and the second property corresponding to the second electrode, the first and second electrodes having substantially same characteristics; determining, using a processor module, a value that is representative at least in part of differences in the first and second properties between the first electrode and the second electrode over the time period; and responding to the determination of the value when the value exceeds a predetermined threshold by at least one of deactivating a continuous analyte monitoring system, displaying an alert, instructing a user to remove a sensor comprising the first electrode and the second electrode from the host, or instructing a user to insert a new sensor comprising a new first electrode and a new second electrode in the host.

In a fourth aspect, a method is provided detecting a sensor failure in a continuous analyte monitoring system implanted in a host, the method comprising: receiving sensor data over a time period from a continuous analyte sensor implanted in the host, the sensor data comprising at least one sensor data point; processing the at least one sensor data point using a first algorithm to determine a first analyte concentration value; processing the at least one sensor data point using a second algorithm to determine a second analyte concentration value, wherein the first algorithm is different from the second algorithm; comparing, using a processor module, the first analyte concentration value to the second analyte concentration value; and identifying a sensor failure if a difference between the first analyte concentration value and the second analyte concentration value exceeds a predetermined amount.

In a fifth aspect, a continuous analyte monitoring system is provided, the system comprising: an electrochemical analyte sensor configured to be implanted in a host and to generate a first signal indicative of a first concentration value of a first analyte in the host; a fiber optic sensor configured to be implanted in the host and to generate a second signal indicative of a second concentration value of a second analyte in the host; and a processor configured to evaluate the first concentration value and the second concentration value to determine a third concentration value.

In an embodiment of the fifth aspect, the system comprises a wire-shaped analyte measuring device, wherein the analyte measuring device comprises an elongated body comprising an elongated core, wherein the elongated core comprises at least a portion of the fiber optic sensor, and wherein the electrochemical analyte sensor is formed onto an outer surface of the elongated core.

In an embodiment of the fifth aspect, the first analyte and the second analyte are same.

In an embodiment of the fifth aspect, the first analyte and the second analyte are glucose.

In an embodiment of the fifth aspect, the first analyte and the second analyte are different.

In a sixth aspect, a continuous analyte monitoring system is provided configured for detecting a sensor failure when implanted in a host, the system comprising: a first electrode configured to receive first sensor data when implanted in a host, wherein the first sensor data are indicative of a property corresponding to the first electrode; a second electrode having substantially same characteristics as the first electrode and configured to receive second sensor data when implanted in a host, wherein the second sensor data are indicative of a property corresponding to the second electrode; and a processor module configured to compare the property corresponding to the first electrode with the property corresponding to the second electrode and to identify a failure in at least one of the first electrode or the second electrode when a property magnitude of the first electrode is different from a property magnitude of the second electrode by a predetermined value.

In an embodiment of the sixth aspect, the property is sensor sensitivity to an analyte.

In an embodiment of the sixth aspect, the property is baseline.

In an embodiment of the sixth aspect, the first electrode is located substantially adjacent to the second electrode.

In an embodiment of the sixth aspect, the first electrode and the second electrode are separated by a distance of less than about 1 mm at a closest proximity.

In an embodiment of the sixth aspect, the first electrode and the second electrode are separated by a distance of less than about 0.5 mm at a closest proximity.

In an embodiment of the sixth aspect, the analyte is glucose.

BRIEF DESCRIPTION OF THE DRAWINGS

These and other features and advantages will be appreciated, as they become better understood by reference to the following detailed description when considered in connection with the accompanying drawings, wherein:

FIG. 3A is a perspective-view schematic illustrating an in vivo portion of a multi-electrode analyte sensor, in another embodiment.

DETAILED DESCRIPTION OF THE PREFERRED EMBODIMENT

Definitions

Figure 1:
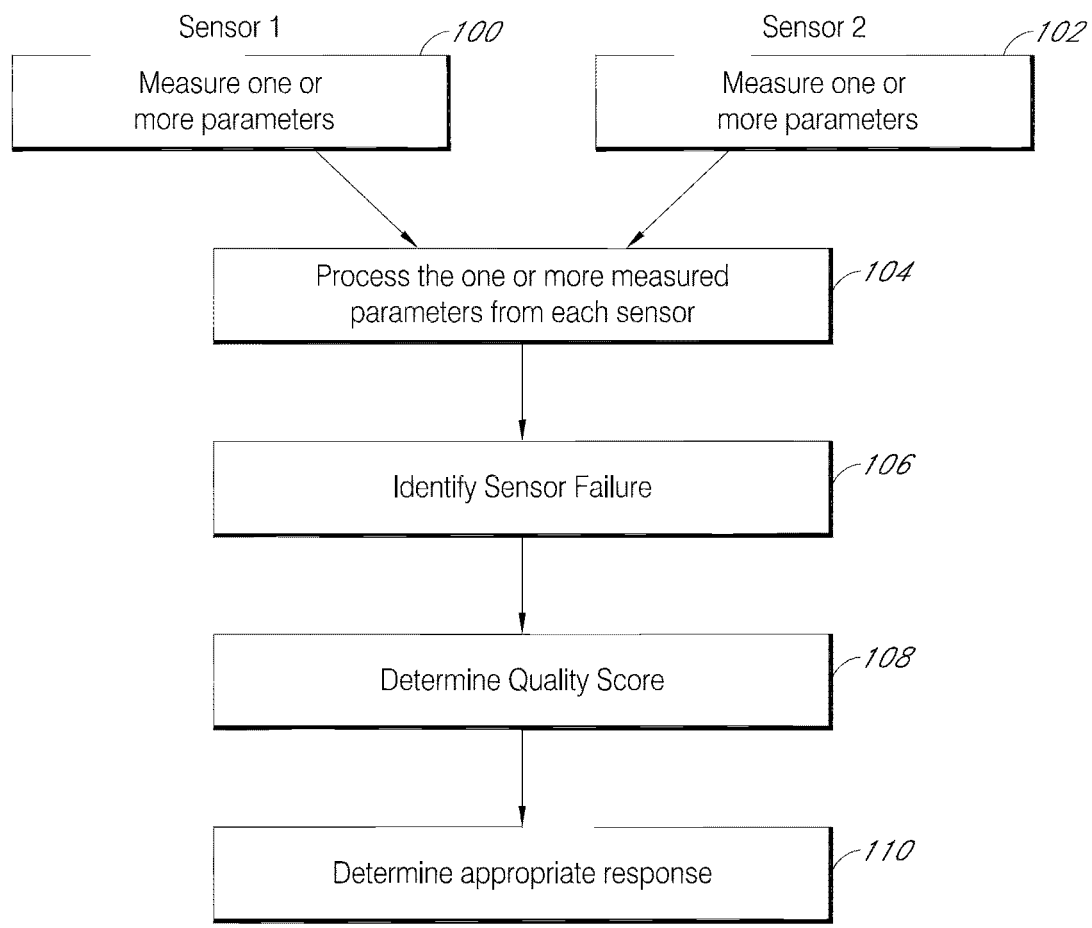
FIG. 1 is a flowchart illustrating a process of measuring, identifying, determining a quality score, and responding steps, in accordance with one embodiment.

In order to facilitate an understanding of the embodiments described herein, a number of terms are defined below.

The term "about," as used herein, is a broad term, and is to be given its ordinary and customary meaning to a person of ordinary skill in the art (and is not to be limited to a special or customized meaning), and when associated with any numerical values or ranges, refers without limitation to the understanding that the amount or condition the terms modify can vary some beyond the stated amount so long as the function of the embodiment is realized.

The term "A/D Converter," as used herein, is a broad term, and is to be given its ordinary and customary meaning to a person of ordinary skill in the art (and is not to be limited to a special or customized meaning), and refers without limitation to hardware and/or software that converts analog electrical signals into corresponding digital signals.

The term "analyte," as used herein, is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; g alacto se-1-pho sphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "baseline," as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal. In certain embodiments, the value of b (i.e., the baseline) can be zero or about zero. This can be the result of a baseline-subtracting electrode or low bias potential settings, for example. As a result, for these embodiments, calibration can be defined by solving for the equation y=mx.

The term "biological sample," as used herein, is a broad term, and is to be given its ordinary and customary meaning to a person of ordinary skill in the art (and is not to be limited to a special or customized meaning), and refers without limitation to sample derived from the body or tissue of a host, such as, for example, blood, interstitial fluid, spinal fluid, saliva, urine, tears, sweat, or other like fluids.

The term "calibration," as used herein, is a broad term, and is to be given its ordinary and customary meaning to a person of ordinary skill in the art (and is not to be limited to a special or customized meaning), and refers without limitation to the process of determining the graduation of a sensor giving quantitative measurements (e.g., analyte concentration). As an example, calibration may be updated or recalibrated over time to account for changes associated with the sensor, such as changes in sensor sensitivity and sensor background. In addition, calibration of the sensor can involve, automatic, self-calibration, that is, calibration without using reference analyte values after point of use.

The term "co-analyte" as used herein is a broad term, and is to be given its ordinary and customary meaning to a person of ordinary skill in the art (and it is not to be limited to a special or customized meaning), and refers without limitation to a molecule required in an enzymatic reaction to react with the analyte and the enzyme to form the specific product being measured. In one embodiment of a glucose sensor, an enzyme, glucose oxidase (GOX) is provided to react with glucose and oxygen (the co-analyte) to form hydrogen peroxide.

The term "comprising" as used herein is synonymous with "including," "containing," or "characterized by," and is inclusive or open-ended and does not exclude additional, unrecited elements or method steps.

The term "computer" as used herein is a broad term, and is to be given its ordinary and customary meaning to a person of ordinary skill in the art (and it is not to be limited to a special or customized meaning), and refers without limitation to machine that can be programmed to manipulate data.

The terms "continuous analyte sensor," and "continuous glucose sensor," as used herein, are broad terms, and are to be given their ordinary and customary meaning to a person of ordinary skill in the art (and are not to be limited to a special or customized meaning), and refer without limitation to a device that continuously or continually measures a concentration of an analyte/glucose and/or calibrates the device (such as, for example, by continuously or continually adjusting or determining the sensor's sensitivity and background), for example, at time intervals ranging from fractions of a second up to, for example, 1, 2, or 5 minutes, or longer.

The phrase "continuous glucose sensing" as used herein is a broad term, and is to be given its ordinary and customary meaning to a person of ordinary skill in the art (and it is not to be limited to a special or customized meaning), and refers without limitation to the period in which monitoring of plasma glucose concentration is continuously or continually performed, for example, at time intervals ranging from fractions of a second up to, for example, 1, 2, or 5 minutes, or longer.

The term "counts," as used herein, is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from a working electrode.

The term "distal" as used herein is a broad term, and is to be given its ordinary and customary meaning to a person of ordinary skill in the art (and it is not to be limited to a special or customized meaning), and refers without limitation to spaces relatively far from a point of reference, such as an origin or a point of attachment.

The term "domain," as used herein, is a broad term, and is to be given its ordinary and customary meaning to a person of ordinary skill in the art (and is not to be limited to a special or customized meaning), and refers without limitation to regions of a membrane that can be layers, uniform or non-uniform gradients (for example, anisotropic), functional aspects of a material, or provided as portions of the membrane.

The term "electrical conductor," as used herein, is a broad term, and is to be given its ordinary and customary meaning to a person of ordinary skill in the art (and is not to be limited to a special or customized meaning) and refers without limitation to materials that contain movable charges of electricity. When an electric potential difference is impressed across separate points on a conductor, the mobile charges within the conductor are forced to move, and an electric current between those points appears in accordance with Ohm's law.

The term "electrical conductance," as used herein, is a broad term, and is to be given its ordinary and customary meaning to a person of ordinary skill in the art (and is not to be limited to a special or customized meaning) and refers without limitation to the propensity of a material to behave as an electrical conductor. In some embodiments, the term refers to a sufficient amount of electrical conductance (e.g., material property) to provide a necessary function (electrical conduction).

The terms "electrochemically reactive surface" and "electroactive surface," as used herein, are broad terms, and are to be given their ordinary and customary meaning to a person of ordinary skill in the art (and they are not to be limited to a special or customized meaning), and refer without limitation to the surface of an electrode where an electrochemical reaction takes place. In one embodiment, a working electrode measures hydrogen peroxide ($H_2O_2$) creating a measurable electronic current.

The term "electrode" as used herein is a broad term, and is to be given its ordinary and customary meaning to a person of ordinary skill in the art (and it is not to be limited to a special or customized meaning), and refers without limitation to a conductor through which electricity enters or leaves something such as a battery or a piece of electrical equipment. In one embodiment, the electrodes are the metallic portions of a sensor (e.g., electrochemically reactive surfaces) that are exposed to the extracellular milieu, for detecting the analyte. In some embodiments, the term electrode includes the conductive wires or traces that electrically connect the electrochemically reactive surface to connectors (for connecting the sensor to electronics) or to the electronics.

The term "enzyme" as used herein is a broad term, and is to be given its ordinary and customary meaning to a person of ordinary skill in the art (and it is not to be limited to a special or customized meaning), and refers without limitation to a protein or protein-based molecule that speeds up a chemical reaction occurring in a living thing. Enzymes may act as catalysts for a single reaction, converting a reactant (also called an analyte herein) into a specific product. In one embodiment of a glucose oxidase-based glucose sensor, an enzyme, glucose oxidase (GOX) is provided to react with glucose (the analyte) and oxygen to form hydrogen peroxide.

The term "filtering," as used herein, is a broad term, and is to be given its ordinary and customary meaning to a person of ordinary skill in the art (and is not to be limited to a special or customized meaning), and refers without limitation to modification of a set of data to make it smoother and more continuous and remove or diminish outlying points, for example, by performing a moving average of the raw data stream.

The term "function" as used herein is a broad term, and is to be given its ordinary and customary meaning to a person of ordinary skill in the art (and it is not to be limited to a special or customized meaning), and refers without limitation to an action or use for which something is suited or designed.

The term "GOx" as used herein is a broad term, and is to be given its ordinary and customary meaning to a person of ordinary skill in the art (and is not to be limited to a special or customized meaning), and refers without limitation to the enzyme Glucose Oxidase (e.g., GOx is an abbreviation).

The term "helix," as used herein, is a broad term, and is to be given its ordinary and customary meaning to a person of ordinary skill in the art (and is not to be limited to a special or customized meaning), and refers without limitation to a spiral or coil, or something in the form of a spiral or coil (such as, for example, a corkscrew or a coiled spring). In one example, a helix is a mathematical curve that lies on a cylinder or cone and makes a constant angle with the straight lines lying in the cylinder or cone. A "double helix" is a pair of parallel helices intertwined about a common axis, such as but not limited to that in the structure of DNA.

The term "host," as used herein, is a broad term, and is to be given its ordinary and customary meaning to a person of ordinary skill in the art (and is not to be limited to a special or customized meaning), and refers without limitation to animals, including humans.

The term "inactive enzyme," as used herein, is a broad term, and is to be given its ordinary and customary meaning to a person of ordinary skill in the art (and is not to be limited to a special or customized meaning), and refers without limitation to an enzyme (such as, for example, glucose oxidase, GOx) that has been rendered inactive (e.g., by denaturing of the enzyme) and has substantially no enzymatic activity. Enzymes can be inactivated using a variety of techniques known in the art, such as but not limited to heating, freeze-thaw, denaturing in organic solvent, acids or bases, cross-linking, genetically changing enzymatically critical amino acids, and the like. In some embodiments, a solution containing active enzyme can be applied to the sensor, and the applied enzyme subsequently inactivated by heating or treatment with an inactivating solvent.

The terms "insulative properties," "electrical insulator," and "insulator," as used herein, are broad terms, and are to be given their ordinary and customary meaning to a person of ordinary skill in the art (and are not to be limited to a special or customized meaning) and refer without limitation to the tendency of materials that lack mobile charges to prevent movement of electrical charges between two points. In one embodiment, an electrically insulative material may be placed between two electrically conductive materials, to prevent movement of electricity between the two electrically conductive materials. In some embodiments, the terms refer to a sufficient amount of insulative property (e.g., of a material) to provide a necessary function (electrical insulation). The terms "insulator" and "non-conductive material" can be used interchangeably herein.

The terms "interferent" and "interfering species," as used herein, are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

The term "in vivo portion" as used herein is a broad term, and is to be given its ordinary and customary meaning to a person of ordinary skill in the art (and is not to be limited to a special or customized meaning), and refers without limitation to a portion of a device that is to be implanted or inserted into the host. In one embodiment, an in vivo portion of a transcutaneous sensor is a portion of the sensor that is inserted through the host's skin and resides within the host.

The term "membrane system," as used herein, is a broad term, and is to be given its ordinary and customary meaning to a person of ordinary skill in the art (and is not to be limited to a special or customized meaning), and refers without limitation to a permeable or semi-permeable membrane that can include two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "operably connected," as used herein, is a broad term, and is to be given its ordinary and customary meaning to a person of ordinary skill in the art (and is not to be limited to a special or customized meaning), and refers without limitation to one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "potentiostat," as used herein, is a broad term, and is to be given its ordinary and customary meaning to a person of ordinary skill in the art (and is not to be limited to a special or customized meaning), and refers without limitation to an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The terms "processor module" and "microprocessor" as used herein are broad terms, and are to be given their ordinary and customary meaning to a person of ordinary skill in the art (and they are not to be limited to a special or customized meaning), and refer without limitation to a computer system, state machine, processor, or the like designed to perform arithmetic and logic operations using logic circuitry that responds to and processes the basic instructions that drive a computer.

The term "proximal" as used herein is a broad term, and is to be given its ordinary and customary meaning to a person of ordinary skill in the art (and it is not to be limited to a special or customized meaning), and refers without limitation to near to a point of reference such as an origin or a point of attachment.

The terms "raw data stream" and "data stream," as used herein, are broad terms, and are to be given their ordinary and customary meaning to a person of ordinary skill in the art (and they are not to be limited to a special or customized meaning), and refer without limitation to an analog or digital signal directly related to the analyte concentration measured by the analyte sensor. In one example, the raw data stream is digital data in counts converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "RAM," as used herein, is a broad term, and is to be given its ordinary and customary meaning to a person of ordinary skill in the art (and is not to be limited to a special or customized meaning), and refers without limitation to a data storage device for which the order of access to different locations does not affect the speed of access. RAM is broad enough to include SRAM, for example, which is static random access memory that retains data bits in its memory as long as power is being supplied.

The term "ROM," as used herein, is a broad term, and is to be given its ordinary and customary meaning to a person of ordinary skill in the art (and is not to be limited to a special or customized meaning), and refers without limitation to read-only memory, which is a type of data storage device manufactured with fixed contents. ROM is broad enough to include EEPROM, for example, which is electrically erasable programmable read-only memory (ROM).

The terms "reference analyte values" and "reference data," as used herein, are broad terms, and are to be given their ordinary and customary meaning to a person of ordinary skill in the art (and they are not to be limited to a special or customized meaning), and refer without limitation to reference data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The term "regression" as used herein is a broad term, and is to be given its ordinary and customary meaning to a person of ordinary skill in the art (and it is not to be limited to a special or customized meaning), and refers without limitation to finding a line in which a set of data has a minimal measurement (for example, deviation) from that line. Regression can be linear, non-linear, first order, second order, and so forth. One example of regression is least squares regression.

The term "sensing region," as used herein, is a broad term, and is to be given its ordinary and customary meaning to a person of ordinary skill in the art (and is not to be limited to a special or customized meaning), and refers without limitation to the region of a monitoring device responsible for the detection of a particular analyte. In one embodiment, the sensing region generally comprises a non-conductive body, at least one electrode, a reference electrode and a optionally a counter electrode passing through and secured within the body forming an electroactive surface at one location on the body and an electronic connection at another location on the body, and a membrane system affixed to the body and covering the electroactive surface.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (such as, for example, $H_2O_2$) associated with the measured analyte (such as, for example, glucose). For example, in one embodiment, a sensor has a sensitivity of from about 1 to about 300 picoAmps of current for every 1 mg/dL of glucose analyte.

The term "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

The terms "sensor analyte values" and "sensor data," as used herein, are broad terms, and are to be given their ordinary and customary meaning to a person of ordinary skill in the art (and they are not to be limited to a special or customized meaning), and refer without limitation to data received from a continuous analyte sensor, including one or more time-spaced sensor data points.

The terms "sensor electronics" and "electronic circuitry," as used herein, are broad terms, and are to be given their ordinary and customary meaning to a person of ordinary skill in the art (and they are not to be limited to a special or customized meaning), and refer without limitation to the components (for example, hardware and/or software) of a device configured to process data. In the case of an analyte sensor, the data includes biological information obtained by a sensor regarding the concentration of the analyte in a biological fluid. U.S. Pat. No. 4,757,022, incorporated herein by reference in its entirety, describes suitable electronic circuits that can be utilized with devices of certain embodiments.

The term "sensor environment" or "sensor operational environment," as used herein, are broad terms and are to be given their ordinary and customary meaning to a person of ordinary skill in the art (and is not to me limited to a special or customized meaning), and refer without limitation to the biological environment in which a sensor is operating.

The terms "substantial" and "substantially," as used herein, are broad terms, and are to be given their ordinary and customary meaning to a person of ordinary skill in the art (and are not to be limited to a special or customized meaning), and refer without limitation to being largely but not necessarily wholly that which is specified.

The term "thermal conductivity," as used herein is a broad term, and is to be given its ordinary and customary meaning to a person of ordinary skill in the art (and it is not to be limited to a special or customized meaning), and refers without limitation to the quantity of heat transmitted, due to unit temperature gradient, in unit time under steady conditions in a direction normal to a surface of unit area.

The term "thermal coefficient," as used herein is a broad term, and is to be given its ordinary and customary meaning to a person of ordinary skill in the art (and is not to be limited to a special or customized meaning), and refers without limitation to the change in resistance of a material at various temperatures.

The term "thermally conductive material," as used herein is a broad term, and is to be given its ordinary and customary meaning to a person of ordinary skill in the art (and is not to be limited to a special or customized meaning), and refers without limitation to materials displaying a high degree of thermal conductivity.

The term "twisted," as used herein, is a broad term, and is to be given its ordinary and customary meaning to a person of ordinary skill in the art (and it is not to be limited to a special or customized meaning), and refers without limitation to united by having one part or end turned in the opposite direction to the other, such as, but not limited to the twisted strands of fiber in a string, yarn, or cable.

Overview

The embodiments described herein relate generally to devices, systems, and methods for processing sensor data and for responding to changes in sensor function. The embodiments described below include one or more sensors configured to provide more reliable continuous glucose or analyte values. In some embodiments, two or more sensors having substantially similar characteristics (e.g., in terms of their function in vivo, e.g., a substantially similar response to a particular analyte and any interferents present in the ambient in vivo environment surrounding the sensors) measure in vivo parameters. In some embodiments, data collected by one or more sensors can be processed by different parallel algorithms. In yet other embodiments, two or more sensors having different characteristics (e.g., a different sensitivity to the same analyte, a different concentration range over which the same analyte can be measured with accuracy, or a different sensitivity to an interferent; such characteristics being due to, e.g., a different chemical composition of the electrode, mode of action, a different membrane system (having different chemistry, porosity, permeability, thickness, hydrophilicity, hydrophobicity, presence or absence of enzyme, presence or absence of additives impacting properties of the membrane or surrounding tissue), a different electroactive surface area, a different surface configuration (e.g., smooth versus rough or porous), a different electrode shape, or the like) can be used to measure in vivo parameters. Such devices, systems, and methods allow for measurement redundancy. Notably, in some embodiments, the devices, systems, and methods can also be used in a manner that provides increased confidence levels in measured parameters or calculated vales (such as, for example, analyte concentration) by providing redundancy. Redundancy can increase confidence in the values obtained; additionally, any deviations between measurements or processing the multiple measurements in certain ways can assist in identifying sensor failure. In turn, information related to sensor performance and identification of sensor failure can provide the user or system with an input (or another input) for determining the appropriate response.

As illustrated in the flowchart of FIG. 1, in one embodiment, the devices and systems described herein can be used to measure an in vivo property, process sensor data, identify a sensor failure, and respond to the sensor failure. Optionally, the system can also be configured to determine a quality score. In some embodiments, as described further below, the measurement data can be processed by electronic circuitry or a processor module in order to identify a sensor failure and/or produce a quality score. In some embodiments, the system can respond to an identified sensor failure in any of a variety of ways. Additionally or alternatively, the system can prompt a user, such as, for example, a patient or doctor, to respond to the sensor failure in any of a variety of ways. The devices, systems, and methods for completing all or some of the steps of FIG. 1 are described further herein.

Although certain sensor configurations are described herein, it should be understood that any of a variety of known sensor configurations can be employed with the analyte sensor systems described herein, such as those described in U.S. Patent Publ. No. 2011-0024307-A1 and U.S. Patent Publ. No. 2011-0027127-A1; which are herein incorporated by reference in their entirety. The sensors described in the above-identified applications are not inclusive of all applicable analyte sensors, however, and it should be understood that the disclosed embodiments are applicable to a variety of analyte sensor configurations.

Two or More Sensors with Substantially the Same Characteristics

Systems including two or more sensors can provide more reliable and accurate continuous analyte values. In certain embodiments, the working electrodes can be fabricated to have substantially the same characteristics such that the system is capable of providing redundant signal measurements. In other embodiments, discussed further below, the sensors of the system can be fabricated with substantially different characteristics or manufacturing specifications. The sensors can be arranged in any of a variety of ways. In one preferred embodiment, the sensors can be configured and arranged for transcutaneous implantation.

Figure 2:
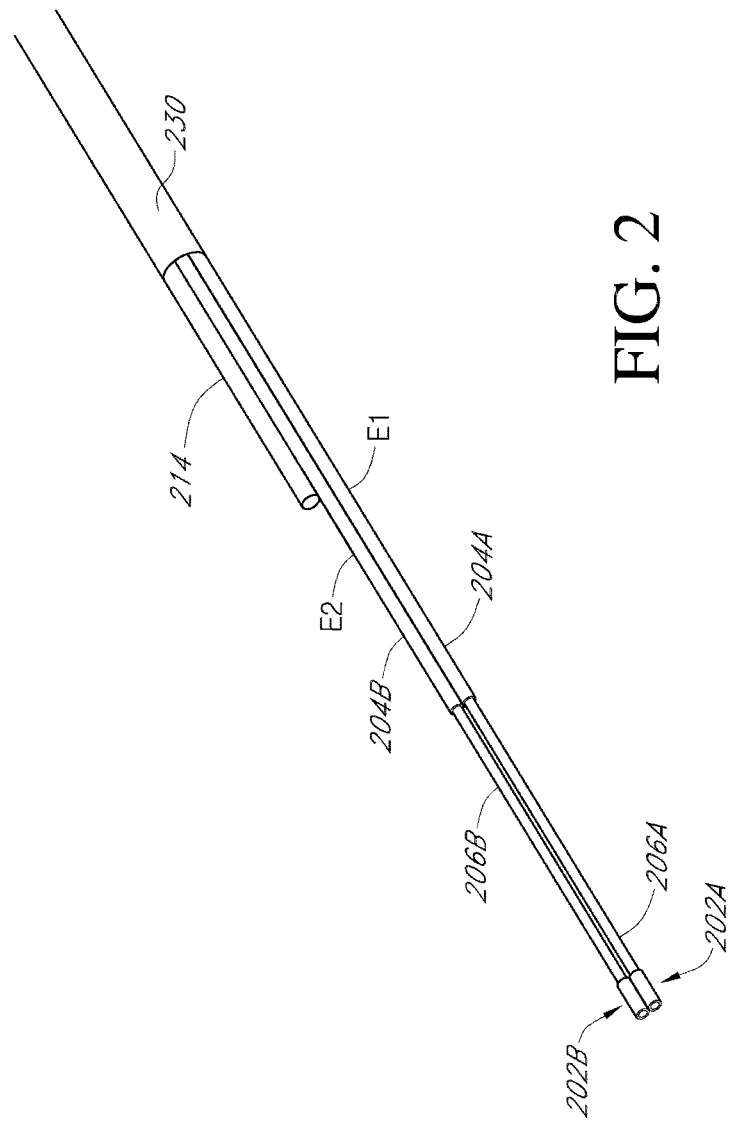
FIG. 2 is a perspective-view schematic illustrating an in vivo portion of a multi-electrode analyte sensor, in one embodiment.

FIG. 2 schematically illustrates the in vivo portion of a dual-electrode analyte sensor, of one embodiment. For example, the sensor can comprise first and second elongated bodies (such as, for example, conductive cores) E1, E2. Further, a working electrode can comprise an exposed electroactive surface of the elongated body and a reference electrode 214. The reference electrode can be bundled together with the first and second elongated bodies E1, E1, for example. Moreover, each working electrode can comprise a conductive core. For example, the first working electrode can comprise an exposed portion of the surface of a first elongated body 202A having an insulating material 204A disposed thereon, such that the portion of the surface of the elongated body (that is, the working electrode) is exposed via a radial window 206A in the insulator. The insulating material 204A can comprise a polymer, such as, a non-conductive (that is, dielectric) polymer. The insulating material can include, for example, at least one of polyurethane, polyimide and parylene. In one embodiment, the insulating material comprises parylene, which can be an advantageous polymer coating for its strength, lubricity, and electrical insulation properties. Generally, parylene is produced by vapor deposition and polymerization of paraxylylene (or its substituted derivatives). However, any suitable insulating material, such as, but not limited to, a dielectric ink, paste or paint, can be used, for example, fluorinated polymers, polyethyleneterephthalate, polyurethane, polyimide, other nonconducting polymers, or the like. In some embodiments, glass or ceramic materials can also be employed.

The elongated body may comprise a core and a first layer, wherein an exposed (that is, electroactive) surface of the first layer is the first working electrode. The second working electrode can comprise an exposed surface of a second core 202B having an insulator 204B disposed thereon, such that a portion of the surface of the core is exposed via a radial window 206B in the insulator. A first layer (not shown) can be applied to the exposed surface of the second core to form the second working electrode. Accordingly, the radial windows can be spaced such that the working electrodes (that is, the electroactive surfaces) are substantially overlapping along the length of the sensor. However, in other embodiments, the working electrodes can be spaced such that they are not substantially overlapping along the length of the sensor. The reference electrode or counter electrode can comprise a wire (such as, for example, Ag/AgCl wire or platinum wire) wrapped around the bundled conductive cores. Alternatively, the reference or counter electrode can comprise a layer of silver-containing material applied to at least one of the elongated bodies E1, E2.

As further shown in FIG. 2, one or more connectors can be configured and arranged to hold the conductive cores and reference electrode together. For example, a tube 230 or heat shrink material can be employed as a connector and/or supporting member. The tubing or heat shrink material may include an adhesive inside the tube so as to provide enhanced adhesion to the components secured within (such as, for example, wire(s), core, layer materials, etc.). In such a configuration, the heat-shrink material functions not only as an insulator, but also to hold the proximal ends of the sensor together so as to prevent or reduce fatigue and/or to maintain the electrodes together in the event of a fatigue failure. The wires need not be a core and a layer, but can instead comprise bulk materials.

The distal ends of the sensor can be loose and finger-like, as depicted in FIG. 2, for example. Alternatively, the distal ends of the sensor can be held together with an end cap. A reference electrode can be placed on one or more of the first and second elongated bodies instead of being provided as a separate electrode, and the first and second elongated bodies including at least one reference electrode thereof can be bundled together. Heat shrink tubing, crimp wrapping, dipping, or the like can be employed to bundle one or more elongated bodies together. In some embodiments, the reference electrode is a wire, such as described elsewhere herein. In other embodiments, the reference electrode comprises a foil. In an embodiment of a dual-electrode analyte sensor, the first and second elongated bodies can be present as or formed into a twisted pair, which is subsequently bundled with a wire or foil reference electrode. Connectors, which can also function as supporting members, can be configured and arranged to hold the conductive cores and reference electrode together.

Figure 3C:
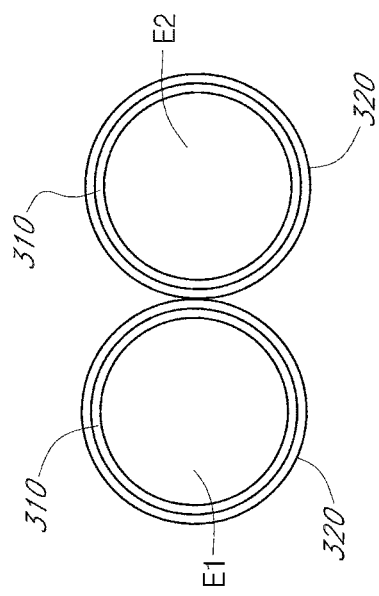
FIG. 3C is a front view of the sensor embodiment illustrated in FIGS. 3A and 3B.
Figure 3B:
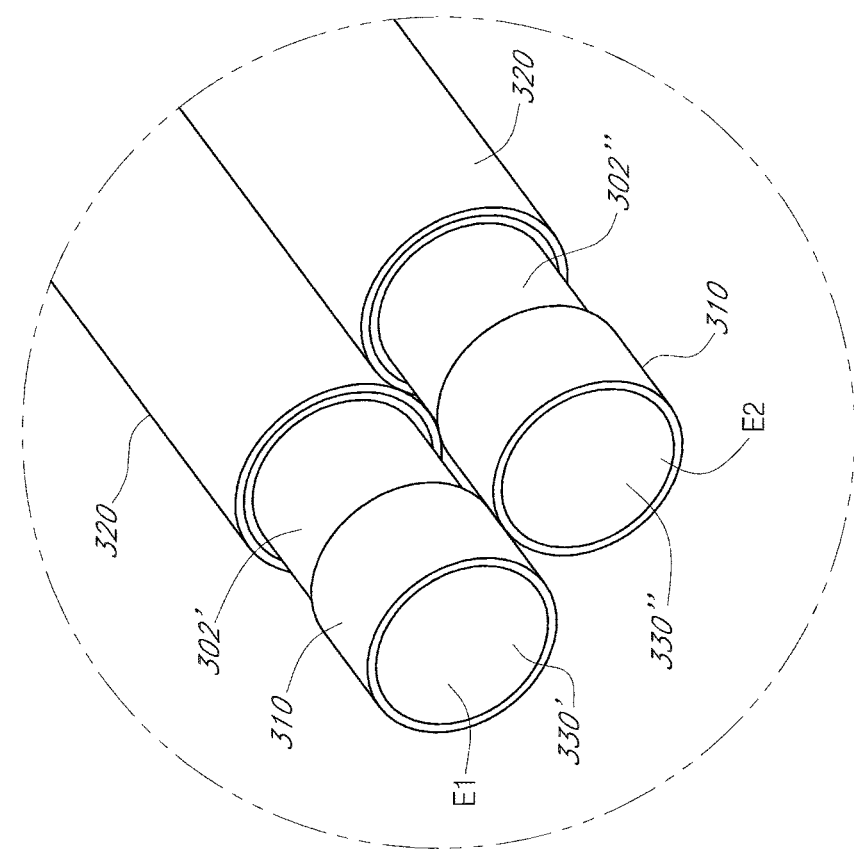
FIG. 3B is a close perspective schematic of the distal portion of the sensor embodiment illustrated in FIG. 3A.

FIG. 3A is a perspective view of the in vivo portion of a multi-electrode sensor system 300. The electrode system 300 may comprise two working electrodes and at least one reference/counter electrode. The sensor system 300 comprises first and second elongated bodies E1, E2. The first and second elongated bodies E1, E2 each can be formed of a conductive core. Alternatively, the first and second elongated bodies E1, E2 can be formed of a core with a conductive layer deposited thereon. As shown in FIG. 3A, for example, an insulating layer 310, a conductive layer 320, and a membrane layer (not shown) can be deposited on top of the first and second elongated bodies E1, E2. The insulating layer 310 can separate the conductive layer 320 from the elongated body. The materials selected to form the insulating layer 310 may include any of the insulating materials described elsewhere herein. For example, the insulating layer can comprise a non-conductive polymer, such as, polyurethane or polyimide. The materials selected to form the conductive layer 320 may include, for example, platinum, platinum-iridium, gold, palladium, iridium, graphite, carbon, a conductive polymer, an alloy, and the like. Working electrodes 302', 302" can be formed by removing a portion of the conductive layer 320 and the insulating layer 310, thereby exposing an electroactive surface of the first and second elongated bodies E1, E2. FIG. 3B provides a close perspective view of the distal portion of the elongated bodies E1, E2. FIG. 3C provides a front view of the sensor illustrated in FIGS. 3A and 3B.

The two elongated bodies illustrated in FIG. 3A can be fabricated to have substantially the same shape and dimensions. The working electrodes can be fabricated to have the same properties, thereby providing a sensor system capable of providing redundancy of signal measurements. In other embodiments, the working electrodes, associated with the elongated bodies E1, E2, may each have one or more characteristics that distinguish each working electrode from the other. For example, in one embodiment, each of the elongated bodies E1, E2 may be covered with a different membrane, so that each working electrode has a different membrane property than the other working electrode. For example, one of the working electrodes may have a membrane comprising an enzyme layer and the other working electrode may have a membrane comprising a layer having either an inactivated form of the enzyme or no enzyme.

Although not shown in FIGS. 3A-3C, the distal ends 330', 330" of the core portions of the elongated bodies E1, E2, respectively, can be covered with an insulating material (such as, for example, polyurethane or polyimide). Alternatively, the exposed core portions 330', 330" can be covered with a membrane system and serve as additional working electrode surface area.

Figure 4A:
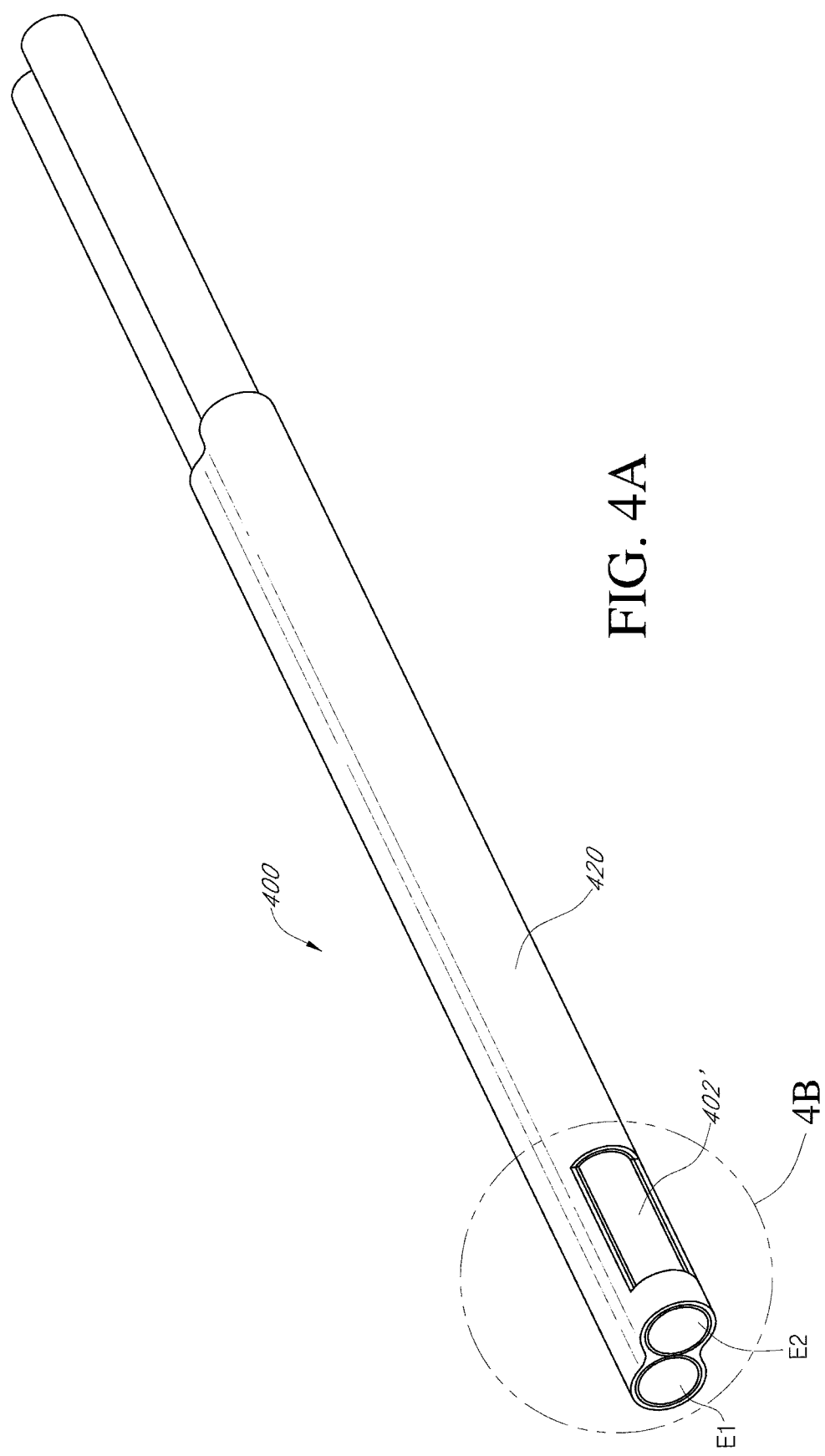
FIG. 4A is a perspective-view schematic illustrating an in vivo portion of a multi-electrode analyte sensor, in another embodiment.
Figure 4C:
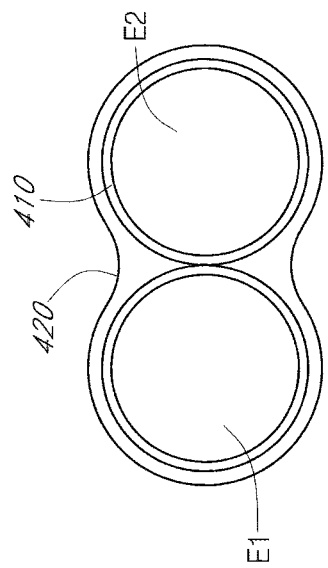
FIG. 4C is a front view of the sensor embodiment illustrated in FIGS. 4A and 4B.
Figure 4B:
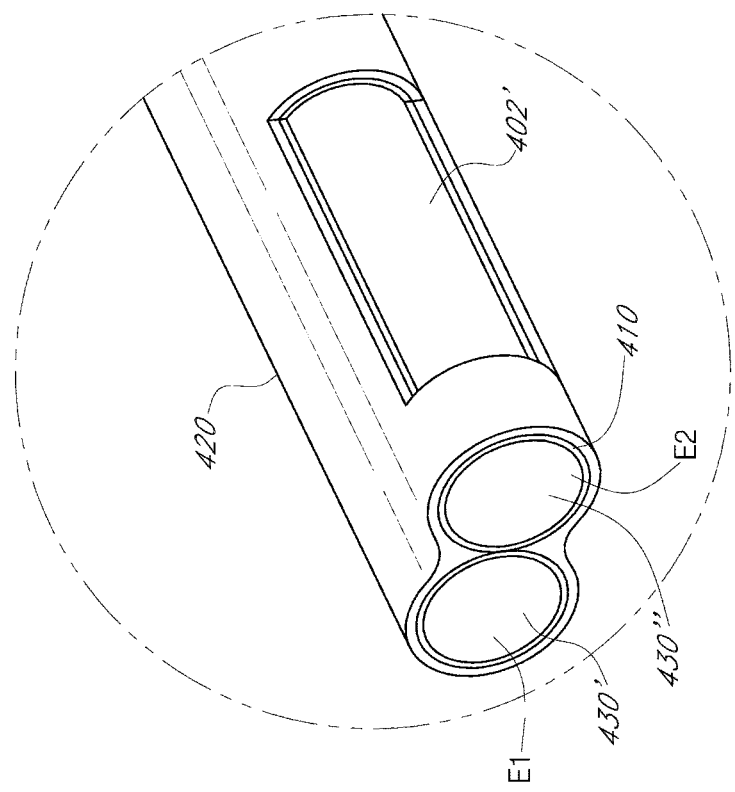
FIG. 4B is a close perspective schematic of the distal portion of the sensor embodiment illustrated in FIG. 4A.

FIG. 4A is a perspective view of the in vivo portion of an embodiment of a multi-electrode sensor system 400 comprising two working electrodes and at least one reference/counter electrode. The sensor system 400 comprises first and second elongated bodies E1, E2. First and second elongated bodies, E1, E2 each can be formed of a conductive core. Alternatively, first and second elongated bodies E1, E2 can be formed of a core with a conductive layer deposited thereon. An insulating layer 410 can be deposited onto each elongated body E1, E2. Furthermore, a conductive domain 420 and a membrane layer (not shown) can be deposited on top of an assembly comprising the elongated bodies E1, E2 and the insulating layer 410. The conductive domain 420 can bind the two elongated bodies E1, E2 into one elongated body. The insulating layers 410 surrounding each elongated body E1, E2 can prevent electrical contact between the two elongated bodies E1, E2. The materials selected to form the insulating layer 410 can include any of the insulating materials described elsewhere herein, including, for example, polyurethane and polyimide. The materials selected to form the conductive domain 420 can include any of the conductive materials described elsewhere herein, including, for example silver/silver-chloride and platinum. Working electrode 402' on elongated body E1 and another working electrode (not shown) on elongated body E2, can be formed by removing a portion of the conductive domain 420 and a portion of the insulating layer 410, thereby exposing electroactive surfaces of elongated bodies E1, E2. The portion of the conductive domain 420 not removed can form the reference/counter electrode. FIG. 4B provides a close perspective view of the distal portion of the elongated bodies E1, E2. FIG. 4C provides a front view of the sensor embodiment illustrated in FIGS. 4A and 4B.

As described elsewhere herein, the working electrodes, associated with the elongated bodies E1, E2, may each have one or more characteristics that distinguish each working electrode from the other. For example, in some embodiments, one of the working electrodes may have a membrane comprising an enzyme layer and the other working electrode may have a membrane comprising a layer having either an inactivated form of the enzyme or no enzyme.

Although not shown in FIGS. 4A-4C, the distal ends 430', 430" of the core portions of the elongated bodies E1, E2, respectively, can be covered with an insulating material (such as, for example, polyurethane or polyimide). Alternatively, one or more of the exposed core portions 430', 430" may be covered with a membrane system and serve as additional working electrodes.

Methods of fabrication of sensor systems such as those illustrated in FIGS. 3A-3C and 4A-4C are described in U.S. Patent Publ. No. 2011-0027127-A1, which is incorporated by reference herein in its entirety.

In some embodiments, a substantial portion of the in vivo portion of the sensor can be designed with at least one dimension less than about 0.004 inches, about 0.005 inches, about 0.006 inches, about 0.008 inches, about 0.01 inches, about 0.012, about 0.015, or about 0.02 inches. In some embodiments, in which the sensor is configured and arranged for implantation into a host vessel, a substantial portion of the sensor that is in fluid contact with the blood flow can be designed with at least one dimension less than about 0.001, about 0.002, about 0.003, about 0.004, about 0.005, about 0.006, about 0.008, about 0.01, about 0.012, or about 0.015, inches. In one embodiment, a sensor can be formed from a 0.004 inch conductive wire (such as, for example, platinum) for a diameter of about 0.004 inches along a substantial portion of the sensor (such as, for example, an in vivo portion or fluid contact portion). In another embodiment, a sensor can be formed from a 0.004 inch conductive wire and vapor deposited with an insulator material for a diameter of about 0.005 inches along a substantial portion of the sensor (such as, for example, an in vivo portion or fluid contact portion), after which a desired electroactive surface area can be exposed. In the embodiments described above with reference to FIGS. 2-4C, the reference electrode can be located remote from the working electrode (e.g., formed from the conductive wire).

Figure 5:
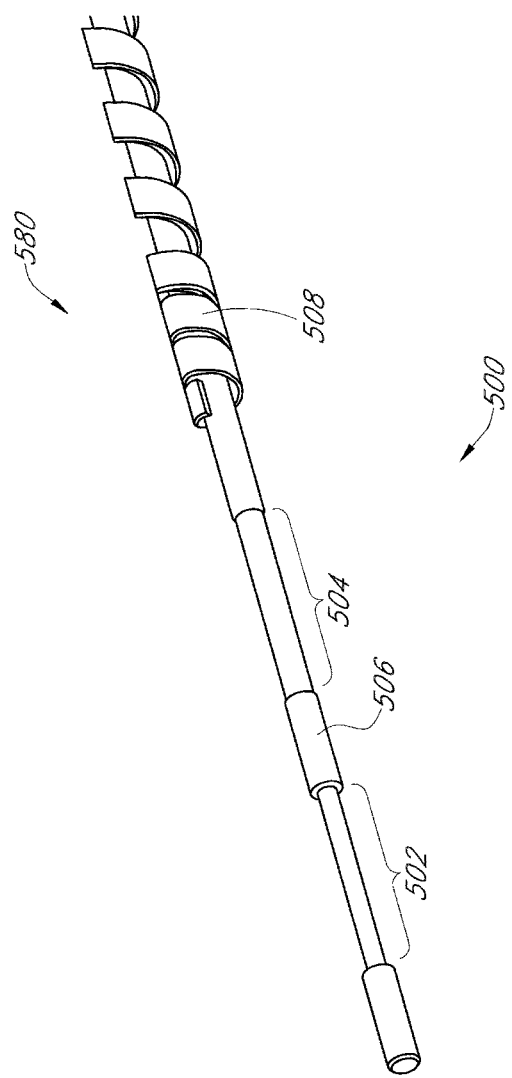
FIG. 5 is a view of one embodiment of a continuous analyte sensor.

As another example, FIG. 5 provides a perspective view of one embodiment of a sensor system 580 and illustrates an in vivo portion of a working electrode 500 comprising two analyte sensors 502 and 504 and a reference electrode 508. While the devices and methods described herein are suitable for use within the host's blood stream, one skilled in the art will recognize that the systems, configurations, methods and principles of operation described herein can be incorporated into other analyte sensing devices, such as but not limited to transcutaneous devices, subcutaneous devices, and wholly implantable devices such as those described in U.S. Patent Publ. No. 2006-0016700-A1, which is herein incorporated by reference in its entirety.

In addition to the embodiments described above, the sensor can be configured with additional working electrodes, as described in U.S. Patent Publ. No. 2005-0143635-A1; U.S. Pat. No. 7,081,195; and U.S. Patent Publ. No. 2007-0027385-A1, each of which is herein incorporated by reference in its entirety. For example, in one embodiment, the sensor comprises an auxiliary working electrode, wherein the auxiliary working electrode includes a wire formed from a conductive material, such as one or more of those described with reference to the glucose-measuring working electrode above. The reference electrode, which can function as a reference electrode alone, or as a dual reference and counter electrode, can be formed from silver, silver/silver chloride, and/or the like.

In some embodiments, the electrodes are juxtapositioned and/or twisted with or around each other; however other configurations are also possible. In one example, the auxiliary working electrode and reference electrode can be helically wound around the glucose-measuring working electrode. Alternatively, the auxiliary working electrode and reference electrode can be formed as a double helix around a length of the glucose-measuring working electrode. The assembly of wires can then be optionally coated together with an insulating material, similar to that described above, in order to provide an insulating attachment. Some portion of the coated assembly structure can then be stripped, for example, using an excimer laser, chemical etching, and the like, to expose the electroactive surfaces. In some alternative embodiments, additional electrodes can be included within the assembly, for example, a three-electrode system (including separate reference and counter electrodes) as is appreciated by one skilled in the art.

In some alternative embodiments, additional electrodes can be included within the assembly, for example, a three-electrode system (working, reference, and counter electrodes) and/or an additional working electrode (such as, for example, an electrode which can be used to generate oxygen, which is configured as a baseline subtracting electrode, or which is configured for measuring additional analytes). Systems and methods for implementing and using additional working, counter, and/or reference electrodes are described in U.S. Pat. No. 7,081,195; A1; U.S. Patent Publ. No. 2005-0143635-A1; and U.S. Patent Publ. No. 2007-0027385-A1, each of which is incorporated by reference in its entirety herein. In one implementation wherein the sensor includes two working electrodes, the two working electrodes are juxtapositioned (such as, for example, extend parallel to each other), around which the reference electrode can be disposed (such as, for example, helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). In certain embodiments, the analyte sensor can be configured as a dual-electrode system and includes a first working electrode and a second working electrode, in addition to a reference electrode. The first and second working electrodes may be in any useful conformation, as described in U.S. Patent Publ. No. 2007-0027385-A1; U.S. Patent Publ. No. 2007-0213611-A1; U.S. Patent Publ. No. 2007-0032717-A1; U.S. Patent Publ. No. 2007-0093704-A1; and U.S. Patent Publ. No. 2008-0083617-A1, each of which is incorporated by reference in its entirety herein. In some embodiments, the first and second working electrodes are twisted and/or bundled. For example, two wire-shaped working electrodes can be twisted together, such as in a helix conformation. The reference electrode can then be wrapped around the twisted pair of working electrodes. In some embodiments, the first and second working electrodes are in a coaxial configuration. In some embodiments, the sensor can be configured as a dual electrode sensor, such as described in U.S. Patent Publ. No. 2005-0143635-A1; U.S. Patent Publ. No. 2007-0027385-A1; U.S. Patent Publ. No. 2007-0213611-A1; and U.S. Patent Publ. No. 2008-0083617-A1, each of which is incorporated by reference in its entirety herein.

In certain embodiments, one or more working electrodes can be associated with one or more membranes or membrane systems. In some embodiments, a first working electrode can be associated with a first membrane system, while a second working electrode can be associated with another membrane system. In some embodiments, the thickness, composition, and/or structure of one or more layers (such as, for example, electrode, interference, or enzyme domains) of a first membrane system can differ from that of a second membrane system, but in other embodiments, the membrane systems may be substantially the same.

The sensor system includes electronics that may be operably connected to the first and second working electrodes. The electronics are configured to provide the first and second signals that are used to generate glucose concentration data and other in vivo data. The electronics can include at least a potentiostat that provides a bias to the electrodes. In some embodiments, sensor electronics are configured to measure the current (or voltage) to provide the first and second signals. The first and second signals are used to determine the glucose concentration and/or other data. The electronics can also apply various data analysis techniques to compare or otherwise assess the signals. In some embodiments, the sensor electronics include a transmitter that transmits the first and second signals to a receiver, where additional data analysis and/or calibration of glucose concentration can be processed. Systems and methods for processing sensor analyte data in general are described in U.S. Patent Publ. No. 2005-0027463-A1; U.S. Patent Publ. No. 2005-0203360-A1; and U.S. Patent Publ. No. 2006-0036142-A1, each of which is incorporated by reference in its entirety herein.

Furthermore, the sensors can be arranged and positioned in any of a variety of ways. In some embodiments having two or more sensors, the electrodes or electroactive surfaces are not in close proximity to each other. For example, in certain embodiments the electrodes can be positioned about 0.01, 0.05, 0.1, or 0.15, or more inches away from each other. In some embodiments, sensors can be configured such that the first and second working electrodes are placed in close proximity to each other such that they are influenced by substantially equivalent in vivo environmental factors. For example, a first electrode can be adjacent to a second electrode, in some embodiments. In some embodiments, the electrodes can be separated by a distance of about 0.01 inches or less. In one embodiment, the dual-electrode sensor can be configured for fluid communication with the circulatory system of the host, such as by implantation in the host's vein or artery via a vascular access device (also referred to as a fluid communication device herein) such as a catheter and/or cannula. When the sensor is contacted with a sample of the host's circulatory system (such as, for example, blood), the first and second working electrodes are configured such that they are influenced by a variety of substantially equivalent environmental factors impinging upon the sensor, such as, but not limited to, non-analyte related electroactive species (such as, for example, interfering species, non-reaction-related $H_2O_2$, another electroactive species). When the first and second working electrodes are influenced by substantially equivalent in vivo environmental factors, as is typically the case when closely spaced together, the signal component associated with the in vivo environmental factors (such as, for example, non-analyte related species with an oxidation/reduction potential that overlaps with that of the analyte) may be removed from the signal detected by the first working electrode (namely, the first signal). This can give a substantially analyte-only signal.

In some embodiments, rather than having two or more separate electrodes formed on multiple different wires, a single wire can be configured to have two or more electroactive surfaces. For example, a single wire can be configured with two or more skived portions, each skived portion corresponding to an electroactive surface. In some embodiments, the skived portions can be separated by a close distance, e.g., up to about 0.001 inches, up to about 0.002 inches, up to about 0.003 inches, up to about 0.004 inches, up to about 0.005 inches, up to about 0.006 inches, up to about 0.007 inches, up to about 0.008 inches, up to about 0.009 inches, about 0.01 inches or more, about 0.02 inches or more, about 0.03 inches or more, about 0.04 inches or more, about 0.05 inches or more, about 0.06 inches or more, about 0.07 inches or more, about 0.08 inches or more, about 0.09 inches or more, about 0.1 inches or more, about 0.2 inches or more, about 0.3 inches or more, about 0.4 inches or more, or about 0.5 inches or more. Furthermore, in some embodiments, the skived portions can be displaced relative to each other along the longitudinal axis of the wire.

In certain embodiments having a skived wire, the electroactive surfaces can be connected by a conductive layer, which allows the signals from the separated electroactive surfaces to be averaged (or aggregated) together to determine analyte values. In other embodiments, however, the electroactive surfaces are not connected by a conductive layer, and thus can serve as two separate electrodes. In some embodiments, one or more electroactive surfaces connected by a conductive layer can form a first group, while one or more additional electroactive surfaces are not connected by the conductive layer. In other embodiments, the multiple electroactive surfaces can be formed into multiple separate groups of connected electroactive surfaces, so that multiple averaged (or aggregated) signals can be used to determine analyte values.

In certain embodiments, a working electrode can have two or more analyte sensor elements. FIG. 5 provides a perspective view of one embodiment of a sensor system 580 and illustrates an in vivo portion of a working electrode 500 having two analyte sensor elements 502 and 504 and a reference electrode 508. The reference electrode 508 can be used to provide a reference value for measuring the working electrode potential of the sensor elements 502, 504. In this particular embodiment, an insulator 506 can be disposed between the two sensor elements 502 and 504, and between the sensor element 504 and the reference electrode 508, to provide electrical insulation therebetween. In some embodiments, the insulator spacing separating the two sensor elements 502 and 504 may be minimized, so that the sensor elements 502 and 504 may both function under almost identical physiological conditions. In certain further embodiments, the insulator spacing can be from about 0.001 to about 100 microns, or from about 0.1 to about 50 microns, or from about 10 to about 25 microns.

Additional sensor systems and configuration are described in the following U.S. Patent Publications, each of which is incorporated by reference in its entirety herein: U.S. Patent Publ. No. 2011-0027127-A1 and U.S. Patent Publ. No. 2011-0024307-A1, each of which is incorporated by reference herein in its entirety. Although the examples provided above describe a sensor system having two or three sensor elements, it is also contemplated that the sensor system can include any number of sensor elements.

Figure 6:
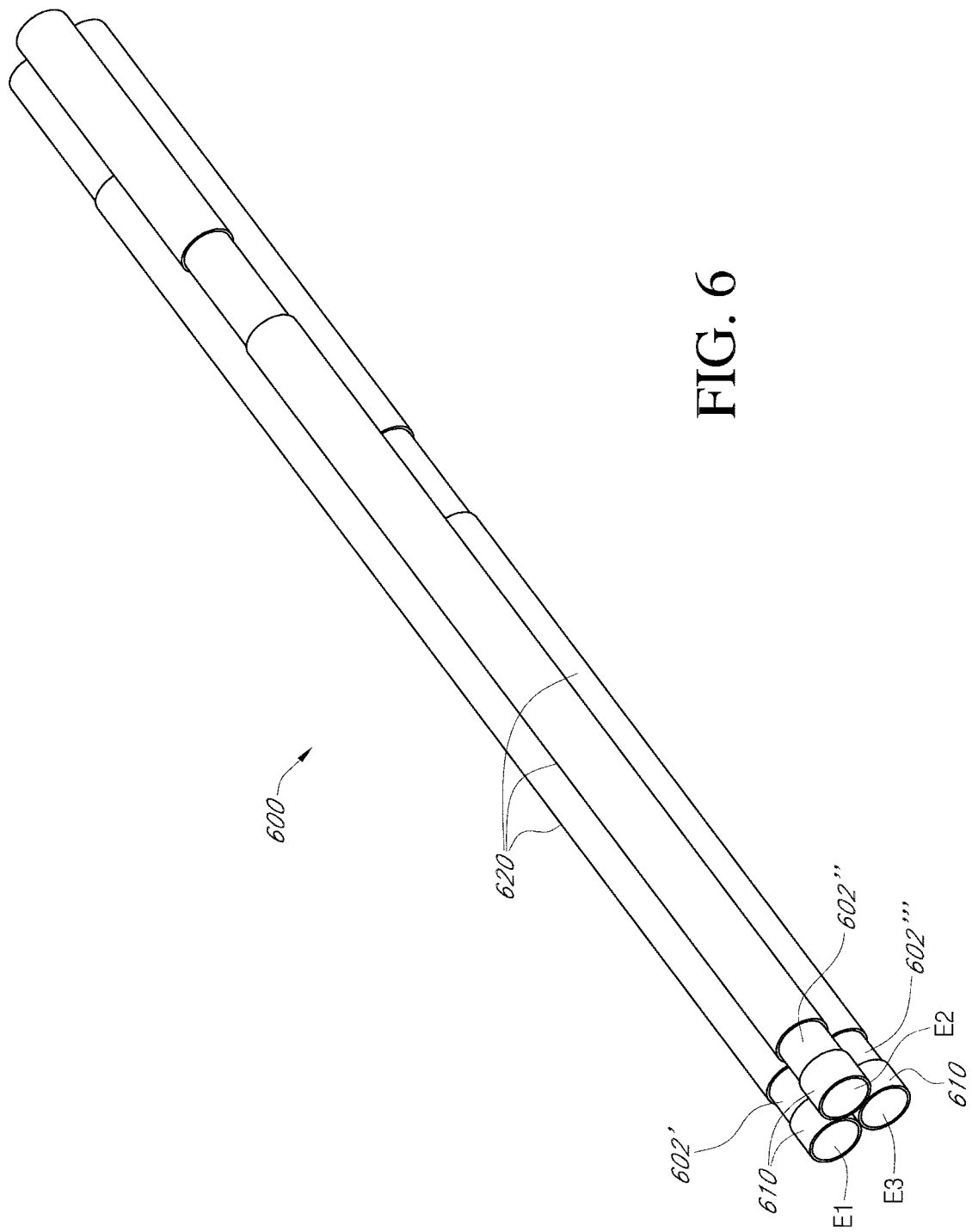
FIG. 6 illustrates one embodiment of a three electrode sensor.

For example, in some embodiments, a tri-filar sensor system 600 is provided. In some embodiments, the tri-filar system 600 can be configured like that shown in FIG. 6. In some embodiments, the sensor system 600 includes three or more working electrodes, which can be integrated into one piece or be separated. For example, the sensor system 600 may have a first, second, and third working electrode 602', 602", 603'''. Moreover, the sensor system 600 can be configured to have characteristics and properties as described above. For example, the sensor system 600 can comprise first, second, and third elongated bodies E1, E2, E3. The first, second, and third elongated bodies E1, E2, E3 each can be formed of a conductive core. Alternatively, the first, second, and third elongated bodies E1, E2, E3 can be formed of a core with a conductive layer deposited thereon. As shown in FIG. 6, for example, an insulating layer 610, a conductive layer 620, and a membrane layer (not shown) can be deposited on top of the first, second, and third elongated bodies E1, E2, E3. The insulating layer 610 can separate the conductive layer 620 from the elongated body. The materials selected to form the insulating layer 610 may include any of the insulating materials described elsewhere herein. For example, the insulating layer can comprise a non-conductive polymer, such as, polyurethane or polyimide. The materials selected to form the conductive layer 620 may include, for example, platinum, platinum-iridium, gold, palladium, iridium, graphite, carbon, a conductive polymer, an alloy, and the like. Working electrodes 602', 602", 602''' can be formed by removing a portion of the conductive layer 620 and the insulating layer 610, thereby exposing an electroactive surface of the first and second elongated bodies E1, E2, E3.

Furthermore, the electrodes can be arranged in any one of a variety of ways. For example, a first, second, and third working electrode 602', 602", 602''' can be twisted or bundled together. In certain embodiments, a first, second, and third working electrode 602', 602", 602''' can be in close proximity so as to be influenced by substantially equivalent in vivo environmental factors. In some embodiments, sensor systems having more than three electrodes can also be used to measure analyte values. For example, in some embodiments, the sensor system can be provided with 4, 5, 6, 7, 8, 9, 10, 20, 40, or more sensor elements.

In some embodiments, the electrodes can be arranged in other ways. In another embodiment, electrodes can be arranged as discs placed linearly along any axis relative to the sensor. In some embodiments, the two or more electrodes can be positioned 0.01, 0.05, 0.1, or 0.15, 0.5, 1, or more inches away from each other. In other embodiments, two or more sensors, each with its own housing or base plate, can be implanted at any location in the abdomen, or other location in the host's body. In some embodiments, the two or more sensor housings can be implanted 0.5, 1, 2, 3, 5, or more inches away from each other.

Systems and Methods for Measurement

Two or more sensors fabricated with substantially similar characteristics or specifications can be used to take various measurements related to sensor function. In some embodiments, each sensor substantially continuously measures an analyte concentration in the host. In some embodiments, a sensor can be programmed to take a measurement upon an external command or user input, such as from a patient or doctor. In some embodiments, a sensor can have a pre-programmed sampling rate, which can be set during the manufacturing process, for example. In other embodiments, a sensor can have a programmed sampling rate that can be set or changed by a user or system inputs before implantation or during use. In some embodiments, for example, the sensor can measure the analyte concentration every fraction of a second, about every fraction of a minute, or every minute. In other embodiments, the sensor measures the analyte concentration at least about every 2, 3, 4, 5, 6, 7, 8, 9, or 10 minutes. In still other embodiments, the sensor measures the analyte concentration every fraction of an hour, such as but not limited to every about 15, 30 or 45 minutes. Yet in other embodiments, the sensor measures the analyte concentration about every hour or longer. In some embodiments, the sensor measures the analyte concentration intermittently or periodically. In one embodiment, the analyte sensor can be a glucose sensor and measures the host's glucose concentration about every 4-6 minutes. In a further embodiment, the sensor measures the host's glucose concentration about every 5 minutes. In some embodiments, other in vivo parameters or sensor properties (such as, for example, sensitivity) can be measured.

The values obtained by each substantially similar sensor can then be compared for consistency. Divergence or variation in values between sensors can indicate that one or more of the sensors may not be working properly. For example, in some embodiments, sensor failure is indicated if the analyte values measured by the sensors vary by more than about 2%. In yet other embodiments, sensor failure is indicated if the analyte values measured by the sensors vary by more than about 3%, 5%, or 10%. In some embodiments, the sensors measure other in vivo parameters or sensor properties (such as, for example, sensitivity, rate of change in sensitivity, current density, change in rate of current density, signal to noise ratio, oxygen level, etc.). In such embodiments, sensor failure can be indicated if the measured values by the sensors of such properties vary by more than about, e.g., 1%, 2%, 3%, 4%, 5%, 6%, 7%, 8%, 9%, or 10% or more.

In some embodiments, a sensor is programmed to sample at a low sample (or sampling) rate, such as, for example, a measurement about every 4, 5, 6, 7, 8, 9, 10, 15, 30, 60 minutes, or longer. In some embodiments, the sample (or sampling) rate of a sensor can be changed to a higher sample rate, such as, for example, a measurement about every 0.1, 0.5, 1, 2, 3, 4, 5, 6, 7, 8, 9, 10, 30, 60, 120, or 180 seconds, by a user or in response to sensor data or inputs (such as, for example, identification of noise or interference activity by the sensor system). In some embodiments, the sample rate of a sensor can be subsequently returned to a low sample rate once noise and/or interference activity levels are at decreased levels. In some embodiments, the sample rate is increased in response to detection of noise. In some embodiments, the sample rate is decreased once the noise is reduced. In some embodiments, a sensor is programmed to sample at a high sample rate, such as, for example, about 10, 30, 60, 120, or 180 seconds, and in certain embodiments, the sample rate of a sensor can be changed to a lower sampling rate, such as, for example, about 5, 10, 15, 30 minutes, or longer, by a user or in response to sensor data or inputs. Higher sample rates typically result in higher temporal resolution of measurements, while higher sample rates can result in more variability. Thus, lower sampling rates may be preferred in some embodiments for detecting divergence between two or more sensors. In some embodiments having two or more sensors fabricated with different characteristics, discussed further below, each sensor can be programmed to sample at a different sample rate. For example, one sensor can be programmed to collect samples at a higher sample rate, such as, for example, every 10, 30, 60, 120, or 180 seconds, while another sensor samples at a lower sample rate, such as, for example, every 5, 10, 15, 30, or more minutes. In another embodiment, one sensor can be programmed to sample every 3, 5, 10, or 15 minutes, while another sensor can be programmed to sample every 30, 45, 60, or more minutes. Many various combinations of sensors having various sample rates are envisioned, and can be used to collect data and provide information on analyte values and other in vivo properties. Additionally, various different filters as are known in the art can be applied to data collected at the various sample rates.

In other embodiments, a processor can also be configured to compare in vivo data (e.g., such as, for example, data relating to sensitivity, current density, etc.) from each sensor to known or prior in vitro data. While not wishing to be bound by theory, it is believed that measurements from each similarly fabricated sensor may vary by the same scale relative to known in vitro data. If both sensors substantially track the known data, the confidence level in the results increases. If one sensor substantially tracks the known data, but the other sensor substantially diverges or varies (such as, for example, by about 1%, 5%, 10%, 15%, 25%, or more) relative to the known in vitro data, the difference can indicate that one or more of the sensors are not working properly.

In other embodiments, the one or more substantially similar sensors are designed to measure an analyte, and a processor module subsequently considers and compares the raw scaled signals from each sensor. In some embodiments, the raw scaled signals are normalized, and then compared. In certain embodiments, the normalized signals are compared continuously or at regular intervals over time. In certain embodiments, a simple linear transform can be applied to the signals.

In some alternative dual-electrode or multi-electrode system embodiments, the analyte sensor can be configured to transmit signals obtained from each electrode separately (such as, for example, without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (such as, for example, without the use of a reference analyte value). In another such example, by comparing fluctuations in the correlating signals over time, changes in sensitivity can be detected and/or measured. Additionally, divergence or deviations between the signals may be indicative that the one or more sensors are failing to work properly. For example, if the signals diverge by, e.g., about 1%, 2%, 5%, 10% or more, the difference can indicate that one or more of the sensors are not working properly.

In some embodiments, a processor module can compare sensor data from a plurality of sensors. For example, the signal amplitudes from a first sensor can be compared to signal amplitudes from a second, third, or other sensor. Accordingly, the sensor system can provide highly accurate measurements of analyte concentration by comparing the plurality of sensor measurements, and any deviations between the signal amplitudes from different sensors can also indicate that one or more sensors is not working properly. For example, if the signal amplitude from the first, second, third, or more sensors diverge by about 1%, 2%, 5%, 10% or more, the difference can indicate that one or more of the sensors is not working properly.

Analyte sensors can also be manufactured to have any of a variety of sensitivities, for example by applying a different enzyme, a different amount of enzyme, or a different amount of a polymer over the enzyme layer. Sensors can also be manufactured to have a very low baseline, such as through application of an interferent blocking polymer to the sensor surface and through other systems and methods described in U.S. Patent Publ. No. 2013-0053665-A1 and U.S. Patent Publ. No. 2013-0053666-A1, which are incorporated herein by reference in their entirety. Additionally, sensors may be responsive to baseline or sensitivity changes over time. In some embodiments, where the sensors are manufactured with the same specifications, sensor performance or failure can be identified by comparing the in vivo sensitivities, baseline, changes in sensitivity, or changes in baseline over time or at a certain time after implantation. In some embodiments the values between sensors are compared. In other embodiments the values of each sensor can be compared to expected known or in vitro values. In other embodiments, the values of each sensor are compared to the other sensor values and to expected known or in vitro values. Any differences or deviations in property values beyond a certain predetermined threshold level between the sensors can indicate that one or more of the sensors may not be working properly. For example, where the sensors have the same manufacturing specifications, if a first sensor is observed to have a first sensitivity and a second sensor is observed to have a substantially different second sensitivity post-implantation, then it is suspected that one or more of the sensors may not be functioning properly.

In some embodiments, where the sensitivity of the sensors can diverge, e.g., by about 1%, 2%, 5%, 10% or more, the difference can indicate that one or more of the sensors are not working properly.

In additional embodiments, the functionality of the sensors can be determined by comparing derivatives of sensor properties or parameters with respective to time or second order derivatives, or by comparing the measured parameters themselves. It is envisioned that any of the measured parameters (e.g., sensitivity, current density) described in this application, and derivatives thereof (e.g., the first order derivative of sensitivity with respect to time, that is, the rate of sensitivity change, the second order derivative of sensitivity with respect to time, etc.), can be used to evaluate the level of functionality of the sensors. In some embodiments, the sensor properties can be mapped or compared to predetermined threshold values. In certain embodiments, comparison of the sensor properties or derivatives thereof, and/or the deviation between values can be used to determine a probability that one or more of the sensors is not functioning properly. For example, if the measured properties or derivatives thereof of one sensor vary by more than about 10% from the value of the second sensor, there may be an about 90% chance that one or more of the sensors is not functioning properly.

Identification of Sensor Failures

By comparing data from the two or more sensors having the same characteristics, various sensor failures can be identified. Any measured parameters described herein, and additional information (such as, for example, time of day or time after implant, etc.) can be considered and compared to identify sensor failure. Any measured parameters described herein, and additional information (such as, for example, time of day or time after implant, etc.) can also be considered and compared to provide information on the reliability of sensor system.

Any reduction in accuracy or reliability beyond a certain predetermined level can be considered sensor failure. Sensor failure can be a temporary failure, or a long-term or permanent failure. Sensor failure can occur due to many conditions or events, such as, for example, moisture ingress, membrane damage, encapsulation and end of life of the sensor, dip and recover failures, and biomaterial buildup or biofouling. Moisture ingress and membrane damage are sensor failures that often occur within the sensor system itself, and can arise due to a variety of reasons. Failures associated with transcutaneous and implantable sensors are often attributed to in vivo properties and physiological responses in surrounding tissues. For example, a reduction in sensor accuracy following implantation of the sensor is one common sensor failure phenomenon commonly observed. This phenomenon is sometimes referred to as a "dip and recover" process. Dip and recover is believed to be triggered by trauma from insertion of the implantable sensor into a patient, and possibly from irritation of the nerve bundle near the implantation area, resulting in a reduction in blood flow to the implantation area. Alternatively, dip and recover may be related to damage to nearby blood vessels, thereby resulting in a vasospastic event. Any local cessation of blood flow in the implantation area for a period of time leads to a reduced amount of glucose in the area of the sensor. During this time, the sensor has a reduced sensitivity and is unable to accurately track glucose. Thus, dip and recover manifests as a suppressed glucose signal. The suppressed signal from dip and recover often appears within the first day after implantation of the signal, most commonly within the first 12 hours after implantation. Importantly, dip and recover normally resolves within 6-8 hours. Identification of dip and recover can provide information to a patient, physician, or other user that the sensor is only temporarily affected (or that there is only a temporary sensor failure) by a short-term physiological response, and that there is no need to remove the implant as normal function will likely return within hours.

Another example of sensor failure due to in vivo properties and physiological responses in surrounding tissues arises when the implantable sensor becomes coated in biological material. During wound healing and foreign body response, the surface of the implantable sensor can become coated in protein or other biological material to such an extent that the sensor is unable to accurately track blood glucose. This sensor failure phenomenon is sometimes called "biofouling," and biofouling often manifests itself as a downward shift in sensor sensitivity over time. Similarly, the implantable sensor can become encapsulated by biological material to such an extent that glucose is no longer transported to the sensor. At this point, the sensor is considered to effectively to be at the end of its sensor life. In some cases, the implantable device can be programmed to correct for errors associated with biofouling and end of life, so that identification of these phenomena aids in providing more accurate glucose data. Identification of these phenomena also generally indicates that the device has failed and should be replaced.

Sensor electronics can be used to consider and compare data from the two or more sensors. Additional data inputs can also be considered, such as for example, time of day, time after implant, or taking measurements with any of a wide variety of other tools (besides sensor components described elsewhere herein), such as using a thermistor to interrogate tissue surrounding one or more sensors. For example, in some embodiments, a thermistor can be used in a "self-heating mode" whereby a thermistor is heated to a specific temperature (such as for example, about 1, 2, 3, 4, 5 or more degrees Celsius above normal temperature, e.g., body temperature, for a period of, e.g., about 1, 2, 3, 4, 5, or more seconds). In some embodiments, the thermistor can be heated in a pattern (such as, for example, a sinusoidal pattern). In some embodiments, the thermistor used has a resistance of from about 1 kOhm to about 2 kOhm. The processor module can process data from the thermistor, and can determine tissue properties or sensor failure based on decrease in temperature or phase changes in tissue surrounding the thermistor as compared with known or expected values. For example, certain decay waveforms indicate the presence of edema or higher blood flow to the sensor area, which in turn indicates encapsulation, inflammation, or compression in the area of the sensor.

In some embodiments, the sensor electronics can be used to determine and identify the type of sensor failure present. The sensor electronics may include a potentiostat, A/D converter, RAM, ROM, transceiver, processor, and/or the like. The potentiostat may be used to provide a bias to the electrodes and to convert the raw data (e.g., raw counts) collected from a sensor to an analyte concentration value (such as, for example, a glucose concentration value expressed in units of mg/dL). The transmitter may be used to transmit a first and second signal (or additional signals) to a receiver, where additional data analysis and/or calibration of analyte concentration can be processed. In certain embodiments, the sensor electronics may perform additional operations, such as, for example, data filtering and noise analysis.

In some embodiments, a processor can be programmed to compare sensor data from multiple sensors. In some embodiments, the processor can compare a magnitude of a parameter measured by a first sensor to the magnitude of a parameter measured by a second sensor. In other embodiments, the processor can be programmed to compare sensor data with expected known or in vitro values. In some embodiments, the processor can compare the magnitude of a parameter measured by a first sensor, and the magnitude of a parameter measured by a second sensor, to known or in vitro values. In certain embodiments, a failure can be identified when the magnitude of a parameter measured by a first electrode is different from the magnitude of a parameter measured by a second electrode by a predetermined amount.

In some embodiments, the processor can identify one data input, or alternatively can identify one or more of the measured parameters described herein. For example, the processor can be programmed to compare the sensitivity of each sensor a certain time or times after implantation. As another example, the processor can compare baseline changes between each sensor and known in vitro baseline values. In yet another example, the processor can be programmed to compare amplitude and sensitivity changes between two or more sensors. In yet another exemplary embodiment, the processor can compare baseline changes between each sensor and a known in vitro value. In some embodiments where multiple measurements are considered, the processor can be programmed to give each measurement an appropriate weight. For example, where it is known that small changes in amplitude (such as, for example, deviations of less than about 5%) correspond with a high probability (such as, for example, 90% or more) of failure, but small changes in baseline (such as, for example, deviations of less than about 5%) correspond with a lower probability (such as, for example, 50% or more) of failure, the processor can be programmed to compare the amplitudes and changes in baseline in a weighted manner. The processor can also be programmed to recognize that one or more deviations over a certain threshold (such as, for example, deviations of about 2%, 5%, 10%, or 25% or more) between each sensor's measurements of various parameters may be indicative of failure. For example, if one, two, three, or more differences (such as, for example, amplitude and changes in sensitivity both vary by over 5%) are detected, then one or more of the sensors can be considered failed, in some embodiments.

Response to Sensor Failures

Once a sensor failure is detected and identified, the sensor system can be programmed to respond in any one of a variety of ways. In some embodiments, the sensor system can provide a quality score, which indicates how closely the two or more sensors track each other. Thus, the quality score can be indicative of sensor reliability, accuracy, and sensor failure. In some embodiments, the quality score can be a numerical value. Although various scales can be used for the quality score, in one embodiment, a score of 100 can indicate perfect tracking for all measured parameters.

Some embodiments can include a closed loop analyte sensor system, wherein the system uses one or more sensors to measure in vivo parameters and calculate analyte values, and wherein the system can deliver an appropriate amount of a fluid to the patient (such as, for example, through a pump). Such closed loop systems can monitor and control analyte values in a host. In some embodiments, the analyte measured is glucose, and the fluid delivered is insulin. In some embodiments of a closed loop system, a quality score can be considered by the system in determining a response. In some embodiments, of a closed loop system, a quality score can be considered by the system to control the analyte to a target value. In other embodiments of a closed loop system, a quality score can be considered by the system to control the analyte to a target range of values. For example, if the quality score is high, a closed loop system can respond by controlling the analyte (such as, for example, glucose) to a target value (such as, for example, 72 mg/dL), in some embodiments. In other embodiments, the system can respond by controlling the analyte (such as, for example, glucose) to a narrow target range (such as, for example, from about 70 mg/dL to about 100 mg/dL). A high quality score value is a relative term and depends on the scale used; however, in one embodiment where 100 indicates perfect tracking, a high quality score may be any score above about 60, 65, 75, 80, 85, 90, or 95.

In some embodiments, for example, if the quality score is at a medium level, the closed loop system can respond by controlling the analyte (such as, for example, glucose) to a broad target range (such as, for example, from about 70 mg/dL to about 1030 mg/dL). A medium quality score value is a relative term and depends on the scale used; however, in one embodiment where 100 indicates a perfect tracking, a medium quality score may be any score between about 20 to about 95, or about 35 to about 85, or about 45 to about 75, or about 55 to about 65, or about 50 or about 60.

In certain embodiments, if the quality score is low, the closed loop system can respond by controlling the analyte (such as, for example, glucose) to a broad target range (such as, for example, from about 65 mg/dL to about 150 mg/dL). In some embodiments, the system can respond by instructing or notifying the user to use alternative methods (such as, for example, fingerstick glucose monitoring method) to monitor analyte levels. The system can also respond by temporarily or permanently suspending the closed loop system, for example. The system can also respond to a low quality score in other various ways, as further described below with respect to sensor failure. A low value is a relative term and depends on the scale used; however, in one embodiment where 100 indicates a perfect tracking, a low quality score may be any score below about 5, 10, 15, 20, 25, 30, 35, 40, 45, or 50.

While the above examples discuss closed loop analyte sensor systems, quality score data can be utilized as part of a semi-closed loop system and by any analyte sensor systems. For example, a semi-closed loop system can operate by suspending fluid delivery when analyte levels are at a certain level or within a certain range of values. In some semi-closed loop systems, the fluid delivered is insulin and the analyte measured is glucose. In some embodiments of a semi-closed loop system, a quality score can be considered by the system in determining a response. In some embodiments, of a semi-closed loop system, a quality score can be considered by the system to control the analyte to a target value. In other embodiments of a closed loop system, a quality score can be considered by the system to control the analyte to a target range of values. In some semi-closed loop systems, the quality score can be considered by the system to suspend delivery of a fluid until measured analyte values are within a certain target range. Quality score data can also be utilized by other analyte sensors, such as, for example, sensors that measure analyte values and/or provide data to a user. In some embodiments, quality score data can be considered by an analyte sensor in determining an appropriate response. For example, in some embodiments, a low quality score (as defined above), can prompt a system to notify or instruct a user to use an alternative analyte sensing method due to sensor failure. In other embodiments, the quality score can be provided to a user to inform the user as to the reliability of sensor data.

The quality score can be calculated in any of a variety of ways. In one embodiment, a parameter measured by a first sensor is compared to a parameter measured by a second sensor parameter. In one embodiment, multiple parameters measured by the first sensor are compared to multiple parameters measured by the second sensor. In certain embodiments, one or more measured of the measured parameters are weighted in calculating the quality score. For example, the magnitude between the two or more sensor's amplitude, sensitivity, change in sensitivity, baseline, change in baseline, or various scaled raw signals can be considered. In some embodiments, an algorithm may be applied to the sensor data to calculate the quality score.

Once calculated, the quality score can be provided to the user or can be used by the system to develop an appropriate response, as described above. In addition to aiding in monitoring and controlling or partially controlling fluid delivery in closed loop or semi-closed loop systems, the quality score can be utilized to determine or select any of a variety of appropriate responses. For example, in some embodiments, the system can automatically shut off the sensor, either temporarily or permanently. Additionally, the system can provide an audible or visual alarm. In some embodiments, the system can provide various audible or visual information, such as a numerical quality score indicator to inform the user as the reliability of the analyte measurements. In some embodiments, the system can provide instructions to the user, such as directing the user to wait an appropriate amount of time or directing the user to change sensors. In some embodiments, the system can provide instructions to the user to use an alternative method to measure analyte values (such as, for example, a fingerstick glucose monitoring method). In other embodiments, the system can respond by re-calibrating or compensating in some way.

In addition to calculating or providing a quality score, in some embodiments, a sensor system can identify a particular type of sensor failure, such as dip and recover, biofouling, or end of life, as described above. When a particular type of sensor failure is identified, the system can respond in a particular way. For example, if dip and recover conditions are identified, the system can notify a user to use another method to monitor blood glucose levels temporarily until the sensor regains full function. For example, the sensor system can notify the user that sensor data are temporarily affected by implantation of the device, and that glucose should be monitored by another method in the interim. In another embodiment, the system can provide information describing the patient's physiological condition. In one embodiment, the system can explain the cause of the interruption in sensor function. In one embodiment, the sensor system can display an estimated time at which the sensor may likely function properly again. In one embodiment, the sensor system can completely cease display of data. In another embodiment, the system can provide a message, sound an alarm, or otherwise notify the user when the dip and recover event has resolved and that the sensor is functioning properly again. In some embodiments, the sensor system can notify or inform the user through a visually displayed message on a user interface, and in other embodiments, the system can notify or inform the user through audible alarms or messages. In some embodiments, the sensor system can notify or inform the user through a combination of both visual and audible alarms or messages.

After certain sensor failures are identified, such as biofouling or encapsulation, the sensor may no longer be reliable, providing inaccurate sensor data. To prevent further use of the unreliable sensor, in some embodiments a user is notified to change the sensor after it has been determined that the sensor should no longer be used. Once it is determined that the sensor should no longer be used, the sensor system can notify a user that a new sensor should be implanted by audibly and/or visually prompting a user to use a new sensor and/or shutting down a display or ceasing to display sensor data on the display, for example. The alarm can also inform the user why sensor reuse may be undesirable, such as potentially providing inaccurate and unreliable sensor readings. Identification of biofouling or end of life can alternatively or additionally cause the sensor system to fully or partially shut down and/or cease display of sensor data on a user interface of the sensor system. Continuing to use the sensor once biofouling or encapsulation resulting in end of life is detected, can be dangerous to the user, because the sensor may provide inaccurate data upon which the user may rely. In some embodiments, the implantable device can also be programmed to correct for errors associated with biofouling and end of life, so that identification of these sensor failures also aids in providing more accurate glucose data.

In some embodiments, a receiver, which can also be referred to as a display device or user interface, can be in communication (e.g., wired or wireless) with an electronics module, which can be within the sensor housing. The receiver can be an application-specific hand-held device, or a general purpose device, such as a personal computer (PC), smart phone, tablet computer, and the like. In one embodiment, a receiver can be in data communication with the sensor housing for receiving sensor data, such as raw and/or displayable data, and include a processing module for processing and/or display the received sensor data. The receiver can also include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver can be programmed to notify or inform the user in the various ways described above, such as, for example displaying messages or visual information, providing audible instructions, and/or sounding alarms.

Sensor Data Processed by Parallel Algorithms

In other embodiments, one or more sensors manufactured with substantially similar characteristics can produce sensor data which can subsequently be processed using two or more parallel algorithms. For example, in some embodiments, a first algorithm processes at least one sensor data point and a second different algorithm processes the at least one sensor data point. Such configuration allows for increased reliability and accuracy of system values, and can help identify sensor failure.

During development of a type of sensor, data can be collected to empirically design various calibration algorithms, as described herein. Such algorithms can include assumptions and conditions that are observed or derived from the collected data. These various algorithms can differ in a number of ways. For example, in one embodiment, one algorithm can be based on a complex equation (such as, for example, Michaelis-Menten equation), while another algorithm can be based on a linear regression. Once a sensor is implanted, the various developed algorithms can be applied to one or more measured parameters. Where two or more algorithms are applied in parallel, the results of the two or more algorithms can be compared to provide information related to sensor failure or to provide information related to the reliability of the results. For example, if the two or more parallel algorithms calculate substantially similar values, the confidence level in the given values can increase. In some embodiments, the values can be considered substantially similar if they vary by less than about of 1%, 2%, 5%, or 10%. In certain embodiments, the amount or percentage of variation in values calculated by the parallel algorithms can be considered in calculating a quality score, which is discussed further below.

In some embodiments, the parallel algorithms can vary in that each algorithm makes estimations based on different factors such as at least one of calibration, run-in time, baseline, filters, spread, age of matched data pairs, sample rate, or a priori estimations. In other words, each algorithm can involve different assumptions with a matched data pair. In some embodiments, the algorithms can additionally apply different weights to the various measured parameters. As described above, if the different algorithms calculate substantially similar values (such as, for example, quality score, glucose level, etc.), the confidence level in the given values can increase.

In certain embodiments, the sensor can be calibrated in the factory prior to implantation, and no (or only one or a few) further calibration(s) would be required during the sensor's life. In other embodiments, the sensor is configured to be calibrated after implantation by using other methods (such as, for example, finger-stick glucose monitoring methods) to detect blood glucose levels. In some embodiments, one algorithm is to determine values based on the factory calibration, while another algorithm is to determine values based on in vivo measurements and related calibrations (such as, for example, finger-stick glucose monitoring methods). As described above, if the two different algorithms calculate the same value (such as, for example, quality score, glucose level, etc.) for one or more of the measured parameters, the confidence level in the calculated value increases.

In some embodiments, the sensor system can be configured to have a fail-safe method, whereby the system is to rely on the more conservative algorithm should the values calculated by the two different algorithms vary. Alternatively or additionally, the fail-safe method may include a requirement for a certain number of blood glucose readings per day (such as, for example, about 1, 2, 3, 4, or more than 4 fingersticks per day). Other appropriate responses to varying values (such as, for example, values that vary by about more than about 2%, 5%, 10%, 15%, 20%, or 25%) produced by the parallel algorithms are similar to the responses described above with respect to two or more similar sensors above, and are discussed more below.

In some embodiments, the algorithms can consider one or more measured parameters or inputs to determine specific sensor failure modes, such as moisture ingress, dip and recover, biofouling, and encapsulation, as described above. For example, the day of the measurement, time of day of the measurement, baseline, sensitivity, raw scaled signal, impedance, and dynamic response can be considered and can be weighted appropriately. In other embodiments, at least three independent parameters are considered in determining the specific sensor failure modes.

In some embodiments, the system may also include a selection algorithm that can determine which algorithm to rely upon in determining a response (such as, for example, in determining which data to display on a receiver). The selection algorithm can be based on criteria such as available reference values, sensor accuracy information, the amount of calibration data available, the estimated amount of signal drift, analyte concentration, or a combination of conditions. For example, in one embodiment, if glucose concentration falls below about 70 mg/dL, the selection algorithm may determine that the system should switch to rely on a different algorithm.

Identification of Sensor Failure

In some embodiments, sensor failure can be indicated by the parallel algorithms calculating substantially different values (such as, for example, values that vary by about more than about 2%, 25, 10%, 15%, 20%, or 25%), as described above. Algorithms can consider any measured parameters described herein, and additional information (such as, for example, time of day or time after implant, etc.) can also be considered. Reduction in accuracy or reliability beyond predetermined threshold level can indicate sensor failure. Sensor failure can be a temporary failure, or a long-term or permanent failure. Sensor failure can occur due to many conditions or events, such as, for example, moisture ingress, membrane damage, encapsulation and end of life of the sensor, dip and recover failures, and biomaterial buildup or biofouling.

The parallel algorithms can consider any type of measured parameter described herein. Furthermore, the parallel algorithms can consider additional data inputs, such as, for example, time of day, time after implant, or taking measurements with other a wide variety of other tools (besides sensor components described elsewhere herein), such as using a thermistor to interrogate tissue surrounding one or more sensors. For example, in some embodiments, a thermistor can be used in a "self-heating mode," whereby a thermistor is heated to a specific temperature (such as for example, 1, 2, 3, 4, 5 or more degrees Celsius above normal temperature for a period of about 1, 2, 3, 4, 5, or more seconds). In some embodiments, the thermistor can be heated in a pattern (such as, for example, a sinusoidal pattern). In some embodiments, the thermistor used has a resistance of from about 1 kOhm to about 2 kOhm. The processor module can process data from the thermistor, and can determine tissue properties or sensor failure based on decrease in temperature or phase changes in tissue surrounding the thermistor as compared with known or expected values. For example, certain decay waveforms indicated the presence of edema or higher blood flow to the sensor area, which in turn indicates encapsulation, inflammation, or compression in the area of the sensor.

Sensor electronics can be used to consider and compare data from the two or more parallel algorithms. Sensor electronics can also separately consider other data inputs described herein such as, for example, data from a thermistor, to identify sensor failure. In some embodiments, such sensor electronics can further be used to determine a quality score. In some embodiments, the sensor electronics can be used to determine and identify the type of sensor failure present. The sensor electronics may include a potentiostat, A/D converter, RAM, ROM, transceiver, processor, and/or the like. The potentiostat may be used to provide a bias to the electrodes and to convert the raw data (e.g., raw counts) collected from a sensor to an analyte concentration value (such as, for example, a glucose concentration value expressed in units of mg/dL). The transmitter may be used to transmit a first and second signal (or additional signals) to a receiver, where additional data analysis and/or calibration of analyte concentration can be processed. In certain embodiments, the sensor electronics may perform additional operations, such as, for example, data filtering and noise analysis.

In some embodiments, a processor can be programmed to apply one or more parallel algorithms to measured parameters. In some embodiments, a processor can compare values calculated by one or more parallel algorithms. In other embodiments, the processor can be programmed to compare values calculated by one or more parallel algorithms with expected known or in vitro values. For example, in some embodiments, the processor can compare the magnitude of a value (such as, for example, analyte concentration) calculated by the first algorithm, and the magnitude of a value (such as, for example, analyte concentration) calculated by the second algorithm, to known or in vitro values. In certain embodiments, a sensor failure can be identified when the magnitude of a value (such as, for example, analyte concentration) calculated by a first algorithm is different from the magnitude of a value (such, as, for example, analyte concentration) calculated by a second algorithm by a predetermined amount. In some embodiments, the processor can process at least one sensor data point using a first algorithm and/or a second algorithm. In some embodiments, the processor can process any one or more of the measured parameters described herein using a first and/or second algorithm. The processor can receive sensor data over a period of time, and the processor can be programmed to compare the values calculated by each algorithm at a certain time or times after implantation. The processor can also be programmed to recognize that one or more deviations over a certain identified threshold (such as, for example, deviations of 5%, 10%, 15%, 20%, or 25% or more) between one or more algorithm's values may be indicative of failure. For example, if one algorithm calculates values that vary by over about 30% or 50% of an expected or in vitro threshold value, then the sensor can be considered failed, in some embodiments.

Response to Error

If the parallel algorithms calculate substantially different results (such as, for example, values that vary by about more than 5%, 10%, 15%, 20%, or 25%), the sensor system can be programmed to respond in any one of a variety of ways, some of which are discussed above with respect to systems using two similar sensors. As previously mentioned, the sensor system can switch to a fail-safe mode or switch to a more conservative algorithm. In some embodiments, where the calculated values substantially differ, the sensor system can identify whether the factory calibration or in vivo calibration is more accurate. In some embodiments, the sensor system can then revert to the more accurate calibration, or the system can revert to the most conservative calibration. In some embodiments, the system can identify outlying data points, for example a finger-stick glucose measurement that is incorrect. For example, error can occur in finger-stick glucose measurements for a variety of reasons, including user error or device error. In various embodiments, systems and methods can identify erroneous data, or outliers, and proceed with the factory calibrated algorithm.

In some embodiments, the system can provide a quality score, which relates to the degree of difference between results of the two algorithms. Thus, the quality score can be indicative of sensor reliability, accuracy, and sensor failure. In some embodiments, the quality score can be a numerical value. Although various scales can be used for the quality score, in one embodiment, a score of 100 can indicate perfect tracking for all measured parameters.

Some embodiments can include a closed loop analyte sensor system, wherein the system uses one or more sensors to measure in vivo parameters and calculate analyte values, and wherein the system can deliver an appropriate amount of a fluid to the patient (such as, for example, through a pump). Such closed loop systems can monitor and control analyte values in a host. In some embodiments, the analyte measured is glucose, and the fluid delivered is insulin. In some embodiments of a closed loop system, a quality score can be considered by the system in determining a response. In some embodiments, of a closed loop system, a quality score can be considered by the system to control the analyte to a target value. In other embodiments of a closed loop system, a quality score can be considered by the system to control the analyte to a target range of values. For example, if the quality score is high, a closed loop system can respond by controlling the analyte (such as, for example, glucose) to a target value (such as, for example, 72 mg/dL), in some embodiments. In other embodiments, the system can respond by controlling the analyte (such as, for example, glucose) to a narrow target range (such as, for example, from about 70 mg/dL to about 100 mg/dL). A high quality score value is a relative term and depends on the scale used; however, in one embodiment where 100 indicates perfect tracking, a high quality score may be any score above about 60, 65, 75, 80, 85, 90, or 95.

In some embodiments, for example, if the quality score is at a medium level, the closed loop system can respond by controlling the analyte (such as, for example, glucose) to a broad target range (such as, for example, from about 70 mg/dL to about 1030 mg/dL). A medium quality score value is a relative term and depends on the scale used; however, in one embodiment where 100 indicates a perfect tracking, a medium quality score may be any score between about 20-95, 35-85, 45-75, 55-65, or about 50 or about 60.

In certain embodiments, if the quality score is low, the closed loop system can respond by controlling the analyte (such as, for example, glucose) to a broad target range (such as, for example, from about 65 mg/dL to about 150 mg/dL). In some embodiments, the system can respond by instructing or notifying the user to use alternative methods (such as, for example, fingerstick monitoring method) to monitor analyte levels. The system can also respond by temporarily or permanently suspending the closed loop system, such as, for example by taking the system out from an automated or semi-automated mode to a manual mode, whereby the user patient makes the decisions. The system can also respond to a low quality score in other various ways, as further described below with respect to sensor failure. A low value is a relative term and depends on the scale used; however, in one embodiment where 100 indicates a perfect tracking, a low quality score may be any score below 5, 10, 15, 20, 25, 30, 35, 40, 45, or 50, in some embodiments.

While the above examples discuss closed loop analyte sensor systems, quality score data can be utilized as part of a semi-closed loop system and by any analyte sensor systems. For example, a semi-closed loop system can operate by suspending fluid delivery when analyte levels are at a certain level or within a certain range of values. In some semi-closed loop systems, the fluid delivered is insulin and the analyte measured is glucose. In some embodiments of a semi-closed loop system, a quality score can be considered by the system in determining a response. In some embodiments of a semi-closed loop system, a quality score can be considered by the system to control the analyte to a target value. In other embodiments of a closed loop system, a quality score can be considered by the system to control the analyte to a target range of values. In some semi-closed loop systems, the quality score can be considered by the system to suspend delivery of a fluid until measured analyte values are within a certain target range. Quality score data can also be utilized by other analyte sensors, such as, for example, sensors that measure analyte values and/or provide data to a user. In some embodiments, quality score data can be considered by an analyte sensor in determining an appropriate response. For example, in some embodiments, a low quality score (as defined above), can prompt a system to notify or instruct a user to use an alternative analyte sensing method due to sensor failure. In other embodiments, the quality score can be provided to a user to inform the user as to the reliability of sensor data.

The quality score can be calculated in any of a variety of ways. In one embodiment, values calculated by one or more parallel algorithms are compared. In certain embodiments, a value calculated by one algorithm is compared to a value calculated by a second algorithm. In some embodiments, electronic circuitry or a processor is configured to compare values calculated by the parallel algorithms and to calculate the quality score.

Once calculated, the quality score can be provided to the user or can be used by the system to develop an appropriate response, as described above. In addition to aiding in monitoring and controlling or partially controlling fluid delivery in closed loop or semi-closed loop systems, the quality score can be utilized to determine or select any of a variety of appropriate responses. For example, in some embodiments, the system can automatically shut off the sensor, either temporarily or permanently. Additionally, the system can provide an audible, tactile, or visual alarm. In some embodiments, the system can provide various audible or visual information, such as a numerical quality score indicator to inform the user of the reliability of the analyte measurements. In some embodiments, the system can provide instructions to the user, such as directing the user to wait for an appropriate amount of time or directing the user to change sensors. In some embodiments, the system can instruct the user to use an alternative method to measure analyte values (such as, for example, a fingerstick glucose monitoring method). In other embodiments, the system can respond by re-calibrating or compensating in some way.

In addition to calculating or providing a quality score, in some embodiments, a sensor system can identify a particular type of sensor failure, such as dip and recover, biofouling, or end of life, as described above. When a particular type of sensor failure is identified, the system can respond in a particular way. For example, if dip and recover conditions are identified, the system can notify a user to use another method to monitor blood glucose levels temporarily until the sensor regains full function. For example, the sensor system can notify the user that sensor data are temporarily affected by implantation of the device, and that glucose should be monitored by another method in the interim. In another embodiment, the system can provide information describing the patient's physiological condition. In one embodiment, the system can explain the cause of the interruption in sensor function. In one embodiment, the sensor system can display an estimated time at which the sensor may likely function properly again. In one embodiment, the sensor system can completely cease display of data. In another embodiment, the system can provide a message, sound an alarm, or otherwise notify the user when the dip and recover event has resolved and that the sensor is functioning properly again. In some embodiments, the sensor system can notify or inform the user through a visually displayed message on a user interface, and in other embodiments, the system can notify or inform the user through audible alarms or messages. In some embodiments, the sensor system can notify or inform the user through a combination of both visual and audible alarms or messages.

After certain sensor failures are identified, such as biofouling or encapsulation, the sensor may no longer be reliable and is providing inaccurate sensor data. To prevent further use of the unreliable sensor, some embodiments notify a user to change the sensor after it has been determined that the sensor should no longer be used. Once it is determined that the sensor should no longer be used, the sensor system can notify a user that a new sensor should be implanted by audibly and/or visually prompting a user to use a new sensor and/or shutting down a display or ceasing to display sensor data on the display, for example. The alarm can also inform the user why sensor reuse may be undesirable, such as potentially providing inaccurate and unreliable sensor readings. Identification of biofouling or end of life can alternatively or additionally cause the sensor system to fully or partially shut down and/or cease display of sensor data on a user interface of the sensor system. Continuing to use the sensor, once biofouling or substantial encapsulation (which will result in end of sensor life) is detected, can be dangerous to the user because the sensor may provide inaccurate data upon which the user may rely. In some embodiments, the implantable device can also be programmed to correct for errors associated with biofouling and end of life, so that identification of these sensor failures also aids in providing more accurate glucose data.

In some embodiments, a receiver, which can also be referred to as a display device or user interface, can be in communication (e.g., wired or wireless) with an electronics module, which can be within the sensor housing. The receiver can be an application-specific hand-held device, or a general purpose device, such as a P.C., smart phone, tablet computer, and the like. In one embodiment, a receiver can be in data communication with the sensor housing for receiving sensor data, such as raw and/or displayable data, and include a processing module for processing and/or display the received sensor data. The receiver can also and include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver can be programmed to notify or inform the user in the various ways described above, such as, for example displaying messages or visual information, providing audible instructions, and/or sounding alarms.

Two or More Sensors with Different Characteristics

The working electrodes of sensors can be configured to have one or more different characteristics. Additional sensor system configurations that are possible with a plurality of working electrodes (e.g., sensor elements) are described in U.S. Patent Publ. 2011-0024307, which is incorporated by reference herein in its entirety. Sensors with different properties can be useful for identifying one or more in vivo conditions within a host and/or for identifying sensor failure.

Systems having sensors with different characteristics can be configured and arranged in any of a variety of ways, including the ways described above with respect to systems having two or more sensors with the same characteristics, and in the ways illustrated in the embodiments of FIGS. 2-5. As described above, in some embodiments, the sensor system includes a plurality of sensor elements, each or some of which has different characteristics to allow each sensor to measure different parameters.

In some embodiments, the plurality of sensor elements may each be tuned to measure at a particular analyte concentration range, tuned to measure at a particular time period during a sensor session, and/or to tuned to measure at any particular range of any of a variety of parameters (such as, for example, parameters relating to concentration of oxygen, concentration of a interferent, etc.). For instance, in some embodiments, the sensor system includes three sensor elements configured to measure a first range, a second range, and a third range. In certain embodiments, a first sensor element can be associated with a range of about 30-90 mg/dL, a second sensor element can be associated with a range of about 80-160 mg/dL, and a third sensor element can be associated with a range of about 140-400 mg/dL. In other embodiments, the sensor system can be provided with about 4, 5, 6, 7, 8, 9, 10, 20, 40, or more sensor elements.

In some embodiments, each sensor can measure different ranges of analyte concentration. For example, the sensor system may include a first sensor element configured to accurately measure analyte concentration in a first range of analyte concentrations and a second sensor element configured to accurately measure analyte concentration in a second range of analyte concentrations. In some embodiments, the sensor system can be configured to measure glucose concentration from about 30 mg/dL or higher, about 40 mg/dL or higher, about 50 mg/dL or higher, about 60 mg/dL or higher, about 70 mg/dL or higher, or about 80 mg/dL to about 200 mg/dL or higher, about 250 mg/dL or higher, about 300 mg/dL or higher, about 350 mg/dL or higher, about 400 mg/dL or higher, about 450 mg/dL or higher, about 500 mg/dL or higher, about 550 mg/dL or higher, or about 600 mg/dL or higher. As described above, in some embodiments, the sensor system can include a plurality of sensor elements configured to measure different analyte concentration ranges, each of which can include a portion of the physiologically relevant range. In some of these embodiments, the different ranges do not overlap, but in other embodiments, the ranges overlap, either partially or entirely. By way of example, in one embodiment, the sensor system includes a first sensor element configured to measure a glucose concentration of from about 30 mg/dL to about 120 mg/dL and a second sensor element configured to measure a glucose concentration of from about 80 mg/dL to about 400 mg/dL, resulting in a partial overlap of measurement ranges of from about 80 mg/dL to about 120 mg/dL. In alternative embodiments, other measurement ranges are contemplated for each of the plurality of sensor elements. For example, in some embodiments, the first sensor element can be configured to measure a glucose concentration of from about 30 mg/dL to about 120 mg/dL, or from about 40 mg/dL to about 100 mg/dL, and the second sensor element can be configured to measure a glucose concentration of from about 60 mg/dL to about 500 mg/dL, or from about 90 mg/dL to about 450 mg/dL.

In some embodiments discussed above, properties such as the sensitivity or current density (namely, sensitivity divided by surface area of the electroactive surface) of one or more of the sensor elements can be substantially higher than the sensitivities or current densities of other sensor elements. In some embodiments, the sensor system includes a first sensor element having a first sensitivity and a second sensor element having a second sensitivity, wherein the first sensitivity can be higher than the second sensitivity. In some embodiments, the first sensitivity can be from about 1 pA/mg/dL to about 100 pA/mg/dL, or from about 1 pA/mg/dL to about 25 pA/mg/dL, and the second sensitivity can be from about 20 pA/mg/dL to about 300 pA/mg/dL, or from about 50 pA/mg/dL to about 100 pA/mg/dL. In some embodiments, the sensor system includes a first sensor element having a first current density and a second sensor element having a second current density, wherein the first current density can be higher than the second current density. In some of these embodiments, the current density of the first element can be from about 3 pA/mg/dL/mm$^2$ to about 325 pA/mg/dL/mm$^2$, or from about 3 pA/mg/dL/mm$^2$ to about 85 pA/mg/dL/mm$^2$, and the current density of the second element can be from about 65 pA/mg/dL/mm$^2$ to about 1,000 pA/mg/dL/mm$^2$, or from about 165 pA/mg/dL/mm$^2$ to about 1,700 pA/mg/dL/mm$^2$.

In some embodiments, the sensor element with the higher sensitivity or higher current density can be used to measure or provide output at low glucose concentration ranges, while the sensor element with the lower sensitivity or lower current density can be used to measure or provide output at high glucose concentration ranges. Advantageously, in some embodiments, improved glucose concentration measurement accuracy at both low and high glucose levels can be achieved by configuring the first sensor element to have a higher sensitivity or higher current density and the second to have a lower sensitivity or lower current density. Accordingly, in some embodiments, a first sensor can have a first higher sensitivity and a second sensor can have a second lower sensitivity, and a processing module can process data from each sensor such that system can provide accurate analyte values over a broader range. Additionally, a sensor with the higher sensitivity also allows detection of encapsulation as the oxygen flow to the electrodes decreases. Thus, a system including one sensor with a higher sensitivity can help detect end of life, which is a permanent sensor failure. In certain embodiments, a first sensor can have a first higher sensitivity and a second sensor can have a second lower sensitivity, and the processor module can be programmed to identify a sensor failure by comparing sensor data with certain data patterns known to correspond to certain sensor failures. Furthermore, upon detection of encapsulation or other sensor failure, the processing of data streams from the various sensors can be adjusted. For example, in some embodiments, in which weighted averages or weighted sums are used to estimate analyte concentration value, sensor data associated with the sensor element configured with a higher sensitivity may be accorded more weight, and sensor data associated with the sensor element(s) with lower sensitivity may be accorded less (or no) weight. In some embodiments, the processing module can process data from the plurality of sensors having different sensitivities to determine a response (such as, for example, any of the responses to sensor failure described herein).

Sensors can also have different membrane systems, and it is contemplated that in some embodiments, the sensor system has a plurality of sensor elements, in which one or more of the sensor elements are configured to have a different membrane system (namely, with different membrane properties) than the other sensor element(s). Membranes can vary in any one of a variety of ways. In some embodiments, by altering the hydrophilic component to hydrophobic component ratio (as determined by weight), membrane properties can be changed. In some embodiments, a membrane can be changed by altering the hydrophilic component to hydrophobic component ratio such that a membrane property changes with respect to various characteristics, such as, for example, permeability of analyte, sensitivity to analyte, permeability of interferents, sensitivity to interferents, permeability to oxygen, expected sensor life, accuracy at certain periods during a sensor session, etc. In some embodiments, the plurality of sensor elements each includes a membrane with a hydrophilic component and a hydrophobic component, with the membrane of each sensor element having a different hydrophilic component to hydrophobic component ratio than the ratio(s) of the membrane(s) of other sensor element(s). In some embodiments, each sensor has a membrane with different characteristics, and the system is configured to measure various parameters, process data from the plurality of sensors having membranes with different characteristics, and identify a sensor failure.

In some embodiments, to overcome potential issues relating to a molar excess of glucose relative to oxygen in a high sensitivity or high current density sensor element, the sensor system can be designed to contain a plurality of sensor elements, each of which can be configured to have different membrane characteristics, with respect to oxygen permeability and/or glucose permeability.

In certain embodiments, the capability to block different interferent can indicate in vivo conditions. It is contemplated that in some embodiments, the membrane system can be provided with an optional interference domain, also referred to as an interference layer, which can substantially reduce the flux of one or more interferents into the electrochemically reactive surfaces. The interference domain may be configured to be much less permeable to one or more of the interferents than to the measured species, such as, for example, the product of an enzymatic reaction that is measured at the electroactive surface(s), such as $H_2O_2$, for example. In turn, the reduction of interferent permeability corresponds to a reduction or a blocking of artificial signals. Some known interferents for a glucose sensor include acetaminophen, lidocaine, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid, for example. Advantageously, the interference domain contemplated in certain embodiments can be configured to improve interferent blocking in certain key ranges (such as, for example, a hypoglycemic range), where a flux of interferents substantially exaggerates the response signal, thereby leading to false or misleading results. This can be achieved by modifying the thickness or composition of the interference domain to obtain an interference domain with the desired properties. Use of an interference domain in the membrane may result in longer membrane diffusion times (such as, for example, about 1 minute, about 5 minutes, about 10 minutes, about 20 minutes, about 30 minutes, or more than about 30 minutes) for the measured species, because of the interference layer's additional thickness to the membrane. Use of the interference domain may also result in increased startup times (such as, for example, about 30 minutes, about 1 hour, about 3 hours, about 6 hours, about 9 hours, about 12 hours, or more than about 12 hours), due to the additional time required for the sensor to hydrate and break in. Accordingly, by building a sensor with two or more different sensor elements, each selected for different measurement ranges, properties, or time periods for startup, the sensor system can be tuned or adjusted with respect to measurement accuracy across a physiological relevant range of glucose concentrations, startup time, diffusional time lags, and the like. In some embodiments, the sensor system includes a first sensor element and a second sensor element, each with different interference domain properties. For example, in some embodiments, the first sensor element can be configured to measure glucose concentrations in hypoglycemic ranges by being formed with an interference layer with an increased thickness to substantially reduce or block the flux of interferents. In contrast, the second sensor element can be configured to measure glucose concentrations in hyperglycemic ranges by being formed without an interference layer, or alternatively by being formed with an interference layer with decreased thickness.

In one embodiment, the interference domain can be formed from one or more cellulosic derivatives. Cellulosic derivatives include, but are not limited to, cellulose esters and cellulose ethers. In general, cellulosic derivatives include polymers such as cellulose acetate, cellulose acetate butyrate, 2-hydroxyethyl cellulose, cellulose acetate phthalate, cellulose acetate propionate, cellulose acetate trimellitate, and the like, as well as their copolymers and terpolymers with other cellulosic or non-cellulosic monomers. Cellulose is a polysaccharide polymer of β-D-glucose.

While cellulosic derivatives are used in some embodiments, other polymeric polysaccharides having similar properties to cellulosic derivatives can also be employed. Descriptions of cellulosic interference domains can be found in U.S. Patent Publ. No. 2006-0229512-A1; U.S. Patent Publ. No. 2007-0173709-A1; U.S. Patent Publ. No. 2006-0253012-A1; and U.S. Patent Publ. No. 2007-0213611-A1.

In some embodiments, other polymer types that can be utilized as a base material for the interference domain include, but are not limited to, polyurethanes, polymers having pendant ionic groups, and polymers having controlled pore size. In one such alternative embodiment, the interference domain includes a thin, hydrophobic membrane that can be non-swellable and restricts diffusion of high molecular weight species. The interference domain in certain embodiments can be permeable to relatively low molecular weight substances, such as hydrogen peroxide, but also restricts the passage of higher molecular weight substances, including glucose and ascorbic acid. Other systems and methods for reducing or eliminating interference species that can be applied to the membrane system are described in U.S. Pat. No. 7,074,307; U.S. Patent Publ. No. 2005-0176136-A1; U.S. Pat. No. 7,081,195; and U.S. Patent Publ. No. 2005-0143635-A1. In some alternative embodiments, a distinct interference domain is not included in the membrane system or is functionally combined with another layer. In some embodiments, the interference domain can be deposited either directly onto the electroactive surfaces of the sensor or onto the distal surface of the electrode domain. It is contemplated that in some embodiments the thickness of the interference domain can be from about 0.01 microns or less to about 20 microns or more. In some of these embodiments, the thickness of the interference domain can be from about 0.01 microns, about 0.05 microns, about 0.1 microns, about 0.15 microns, about 0.2 microns, about 0.25 microns, about 0.3 microns, about 0.35 microns, about 0.4 microns, about 0.45 microns, about 0.5 microns, about 1 micron, about 1.5 microns, about 2 microns, about 2.5 microns, about 3 microns, or about 3.5 microns to about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, or about 19.5 microns. In some embodiments, the thickness of the interference domain is from about 0.2 microns, about 0.4 microns, about 0.5 microns, or about 0.6 microns to about 0.8 microns, about 0.9 microns, about 1 micron, about 1.5 microns, about 2 microns, about 3 microns, or about 4 microns.

In some embodiments, the sensor system includes a plurality of sensor elements, each with different interference domain properties. It has been found that certain interference domains lack completely precise specificity with respect to interferents. In other words, with certain interference domains, the membrane not only reduces the flux of interferents, but also reduces the flux of glucose or measured species such as hydrogen peroxide generated from an enzyme-catalyzed reaction. In these embodiments, having an interference domain that substantially reduces the flux of an interferent may result in a sensor element with decreased sensitivity and a lower signal level than an equivalent sensor element without the interference domain. In view of the tradeoff that exists in certain interference domains between sensor sensitivity and interference blocking capability, it is contemplated that in certain embodiments, the sensor system may include a plurality of sensor elements, with each having different levels of interference blocking capabilities and/or having specificity for different interferents. Alternatively or additionally, the plurality of sensor elements may each have different specificity for different interferents. In one embodiment, the sensor system may include a first sensor element that has an interference domain specifically designed to substantially reduce (or block) the flux of a certain interferent (such as, for example, acetaminophen), a second sensor element that has a different interference domain specifically designed to substantially reduce (or block) the flux of another interferent (such as, for example, uric acid), a third sensor element that has yet another different interference domain specifically designed to substantially reduce (or block) the flux of yet another interferent (such as, for example, ascorbic acid), and a fourth sensor element that has no interference domain.

Detection of an elevated level of one or more interferents may be obtained by comparing signals associated with the different sensor elements. In certain embodiments, a first sensor can have a first interferent layer, and a second sensor can have a second interferent layer, and the processor module can be programmed to identify the presence of interferents by comparing sensor data with certain data patterns known to correspond to the presence of interferents. Upon detection of elevated levels of one or more interferents, processing of the plurality of data streams associated with their respective plurality of sensor elements may be adjusted. For example, in embodiments in which weighted averages or weighted sums are used to estimate analyte concentration value, sensor data associated with the sensor element configured with a higher interferent blocking ability may be accorded more weight, and sensor data associated with the sensor element(s) without or with minimal interferent blocking ability may be accorded less (or no) weight. In some embodiments, the processing module can process data from the plurality of sensors having different membranes or having different interferent blocking abilities to determine a response (such as, for example, any of the responses to sensor failure described herein).

In some embodiments, the sensor system includes a plurality of sensor elements used to continuously provide sensor data after insertion of the sensor, even during time periods which may be problematic for conventional sensors. In some of these embodiments, the sensor system includes a first sensor element and a second sensor element, each with different membrane properties. The first sensor element can be tuned to measure analyte concentration during a first period, such as an initial time period after sensor implantation (such as, for example, during about the first 0.1 hour, about 0.2 hour, about 0.5 hour, about 0.75 hour, about 1 hour, about 2 hours, about 3 hours, about 6 hours, about 12 hours, about 1 day, about 2 days, about 3 days, about 4 days, about 5 days, about 6 days, or about 7 days post-insertion). In certain embodiments, the first sensor element can be designed with a particular membrane (such as, for example, a membrane that hydrates quickly after insertion into interstitial fluid) that can be tuned for accuracy during the initial period after sensor insertion. The second sensor element can be tuned to measure analyte concentration during a second time period (such as, for example, after about 0.2 hour, about 0.5 hour, about 0.75 hour, about 1 hour, about 2 hours, about 3 hours, about 6 hours, about 12 hours, about 1 day, about 2 days, about 3 days, about 4, days, about 5 days, about 7 days, about 2 weeks, or about 1 year post-insertion), where the second period begins after the initial period begins. In some embodiments, the time periods of the different sensor elements overlap. As described herein elsewhere in more detail, by varying the membrane properties of a sensor element, sensor elements can be tuned to measure accurately over a specific time period. In some embodiments, the time periods can overlap at least partially, but in other embodiments, the time periods do not overlap. In one embodiment of a sensor system with partial overlap of time periods, the first time period can be from about hour-0.2 to about day-3 post-insertion, and the second time period can be from about hour-6 to about day-10 post-insertion. Thus, in this particular example, a partial overlap exists between hour-6 and day-3 post-insertion. Other examples include, for example, but are not limited to, a sensor system having the first time period of from about day-1 to about day-21 post-insertion, and a second time period of from about day-10 to about year-one post-insertion. In yet another embodiment, the time period of one sensor may completely overlap the time period of another sensor. In an embodiment of a sensor system having complete overlap of time periods, the first time period can be from about hour-0.5 to about day-2 post-insertion, the second time period can be from about hour-6 to about day-10 post-insertion, and the third time period can be from about day-3 to about day-10 post-insertion. In this particular example, the second time period completely overlaps the third time period. In some embodiments, the second sensor element tuned to measure at a later time period may be formed with a robust biointerface to create strong vascularized tissue ingrowth, thereby providing more durability, but also a longer break-in time. By having a plurality of sensor elements tuned to different time periods, the sensor system can be capable of continuously and accurately measuring analyte concentrations across a wide range of time periods.

Accordingly, in some embodiments, a first sensor can measure parameters during a first time period, and a second sensor can measure parameters during a second time period, and a processing module can process data from each sensor such that system can provide accurate values (such as, for example, glucose concentration) over a broader time period. In some embodiments, the processing module can process data from a plurality of sensors measuring parameters over different time periods to determine a response (such as, for example, any of the responses to sensor failure described herein).

Additionally, in some embodiments, a multi-sensor system can have at least one working electrode that is configured to measure constant analytes (such as, for example, uric acid), which in turn can provide information on sensor failure and/or in vivo conditions such as dip and recover, biofouling, or encapsulation. Such information can also provide information related to reliability of sensor data. In some embodiments, a working electrode can be configured to generate via sensor electronics a first signal associated with both the analyte and another non-analyte (or second analyte) electroactive compounds that have an oxidation potential less than or similar to a first oxidation potential. An auxiliary electrode can be configured to generate a second signal associated with the non-analyte related electroactive compounds. Non-analyte related electroactive compounds can be any compound, present in the sensor's local environment, which has an oxidation potential less than or similar to the oxidation potential of the measured species (such as, for example, $H_2O_2$). While not wishing to be bound by theory, it is believed that with a glucose-measuring electrode, both the signal directly related to the enzyme-catalyzed reaction of glucose (which produces $H_2O_2$ that is oxidized at the first working electrode) and signals from unknown compounds that are in the extracellular milieu surrounding the sensor can be measured. Additional electrodes or sensors can also measure other various analytes and electroactive compounds. These analytes and compounds can be constant or non-constant (such as, for example, intermittent or transient) in concentration within the body. Measuring changes in a constant analyte can assist in identifying particular physiological conditions and sensor failures.

Second analytes or nonanalytes can be measured in a variety of ways. For example, in a glucose sensor, a non-glucose constant analyte can be measured, wherein the signal can be measured beneath the membrane system on the glucose sensor. While not wishing to be bound by theory, it is believed that by monitoring the sensitivity over a time period, a change associated with solute transport through the membrane system can be measured and used as an indication of a sensitivity change in the analyte measurement. In other words, a biointerface monitor can be provided, which can be capable of monitoring changes in the biointerface surrounding an implantable device, thereby enabling the measurement of sensitivity changes of an analyte sensor over time.

In some embodiments, the analyte sensor can be provided with an auxiliary electrode configured as a transport-measuring electrode disposed beneath the membrane system. The transport-measuring electrode can be configured to measure any of a number of substantially constant analytes or factors, such that a change measured by the transport-measuring electrode can be used to indicate an unusual change in analyte surrounding the sensor. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time, as well as unusual in vivo conditions.

A variety of devices, systems and methods can utilize changes in constant analytes and compounds to identify physiological responses and conditions around the sensor. Because one expects certain analytes to have a constant concentration in the body, a change indicates that the host may be reacting or that the physiological environment around the sensor may be changing. For example, uric acid is expected to remain relatively constant in the host. Changing measurements of a constant analyte, such as uric acid, therefore, can indicate that a physiological event such as dip and recover or encapsulation is occurring.

In one embodiment of a glucose sensor, the transport-measuring electrode can be configured to measure urea, a water-soluble constant analyte known to react directly or indirectly at a hydrogen peroxide sensing electrode (similar to the working electrode of the glucose sensor example described in more detail above). In one implementation wherein urea is directly measured by the transport-measuring electrode, the glucose sensor includes a membrane system as described in more detail above, however, does not include an active interference domain or active enzyme directly above the transport-measuring electrode, thereby allowing the urea to pass through the membrane system to the electroactive surface for measurement thereon. In alternative embodiments wherein urea is indirectly measured by the transport-measuring electrode, the glucose sensor includes a membrane system as described in more detail above, and further includes an active uricase oxidase domain located directly above the transport-measuring electrode, thereby allowing the urea to react at the enzyme and produce hydrogen peroxide, which can be measured at the electroactive surface thereon.

Detection of abnormal levels of constant analytes may be achieved by comparing signals associated with the different sensor elements. In certain embodiments, a first sensor can be configured to measure a constant analyte (such as, for example urea or uric acid), and a processor module may be programmed to determine abnormal concentrations of the constant analyte by comparing sensor data with certain data patterns known to correspond to the analyte. In certain embodiments, a plurality of sensors can be configured to measure one or more constant analytes (such as, for example urea or uric acid), and a processor module may be programmed to determine abnormal concentrations of the one or more constant analytes by comparing sensor data with certain data patterns known to correspond to the analyte. Upon detection of abnormal levels of one or more constant analytes, processing of the data streams associated with their respective sensor element may be adjusted. In some embodiments, the processing module can process data from one or more sensors configured to measure one or more constant analytes to determine a response (such as, for example, any of the responses to sensor failure described herein).

In some embodiments, a multi-sensor system can have at least one working electrode that can be configured as an oxygen sensor. While not wishing to be bound by theory, it is believed that oxygen availability typically decreases with time during the age of a sensor, as the amount of oxygen that can be transported across the membrane of a sensor element diminishes. While not wishing to be bound by theory, it is believed that this phenomenon may be attributed at least in part to the body's response to a foreign object (such as, for example, a continuous glucose sensor), whereby barrier cells are formed surrounding the sensor elements. In turn, the barrier cells reduce or completely block the transport of oxygen across the membrane of the sensor elements. In some embodiments, the sensor system can be formed with a high sensitivity or high current density sensor element that provides greater accuracy during a large duration of the sensor system's life, and a low sensitivity or low current density sensor element that provides better low oxygen performance, and thus can be used near the end of the sensor system's life.

In one embodiment of a glucose sensor, a non-glucose constant that can be measured is oxygen, wherein a measured change in oxygen transport can be indicative of a change in the sensitivity of the glucose signal. Such a change can also be indicative of a physiological response or condition in the body, or indicate sensor failure. The oxygen level can be measured using any one of a variety of devices, systems, and methods, including those known to those of skill in the art. In some particular embodiments, a sensor system can measure the oxygen level by switching the bias potential of the working electrode, using an auxiliary oxygen-measuring electrode, or an oxygen sensor, or the like. Alternatively, oxygen can be measured using pulsed amperometric detection on the glucose-measuring working electrode (eliminating the need for a separate auxiliary electrode). In another embodiment, the auxiliary electrode can be configured specifically as an oxygen-measuring electrode. In another embodiment, an oxygen sensor can be added to the glucose sensor, as appreciated by one skilled in the art, eliminating the need for an auxiliary electrode.

Some preferred embodiments can use the existing structure of a dual or multi electrode analyte sensor, such as those described above, to measure oxygen levels. Glucose oxidase based sensors are limited by the amount of oxygen present. When the oxygen level reduces below a threshold value, the enzyme electrode current drops ("oxygen starvation") while the glucose concentration is constant; therefore, oxygen starvation results in reduced accuracy as lower than actual glucose values are reported by the sensor system. Oxygen starvation can occur when the sensor becomes encapsulated in the subcutaneous environment, for example. Thus, separately measuring oxygen levels at the sensor allows for identification of encapsulation.

Detection of decreasing oxygen values may be obtained by considering signals associated with oxygen sensor element over time. In certain embodiments, the processor module may be programmed to identify a low oxygen level by comparing sensor data with certain data patterns known to correspond to expected or in vitro oxygen levels. Upon detection of decreasing oxygen levels or upon detection of oxygen below a predetermined threshold, processing of the data streams associated with the sensor elements may be adjusted. For example, in embodiments in which weighted averages or weighted sums are used to estimate analyte concentration value, sensor data associated with the sensor element showing normal oxygen levels (or data from any collocated sensor) may be accorded more weight, and sensor data associated with the sensor element showing decreasing or low oxygen levels (or data from any collocated sensor) may be accorded less (or no) weight. In some embodiments, the processing module can process data from the one or more sensors measuring oxygen levels to determine a response (such as, for example, any of the responses to sensor failure described herein).

In some embodiments, each of a plurality of sensor elements can have a different bias potential applied against it by a potentiostat, which can enable measurement of different analytes. For example, an increased bias potential applied against a sensor element may not only facilitate the oxidization and measurement of $H_2O_2$, but may also facilitate the oxidization of water or other electroactive species. In one example, the bias setting can be increased by about 50 mV to about 400 mV above what is typically provided for sufficient $H_2O_2$ measurements. By increasing the bias potential, an electrolysis reaction of water (and possibly other electroactive species) may be carried out, whereby oxygen is produced at the electroactive surface of sensor element. The oxygen produced then diffuses in various directions, including up to the glucose oxidase directly above the electroactive surface. This production of oxygen increases sensor function, particularly in low oxygen environments.

In some embodiments, the sensor system can include a first sensor element configured with a first bias setting (for example, 600 mV) for measuring a signal only from the product of the enzyme reaction, and a second sensor element configured with a second bias setting (for example, +1.0V) that oxidizes and measures water or other electroactive species. In this embodiment, the first sensor element can be configured to measure at low analyte ranges, where the oxygen-to-glucose molar ratio is high, and the second element can be configured to measure at high analyte ranges, where the oxygen-to-glucose molar ratio is low and where additional oxygen can be helpful for preventing a molar excess of glucose relative to oxygen.

In order to use the non-enzyme electrode as an oxygen sensor, in some embodiments, the bias potential of the non-enzyme electrode can be changed from a positive value (typically about 600 mV to about 800 mV) to a negative value (typically about negative 600 mV to negative 800 mV). At this potential, dissolved oxygen can be reduced, giving rise to a negative current through the non-enzyme electrode. Switching the bias potential in this manner results in a bifunctional electrode. When the positive bias is applied, the current is related to a baseline current. When the negative bias is applied, the current is related to the local oxygen concentration.

In yet another embodiment, a negative bias potential can be applied to the non-enzyme electrode and the local oxygen concentration can subsequently be intentionally depleted. Depletion can occur as oxygen is electrochemically removed as a result of the oxygen measurement process, and the enzyme electrode measuring the glucose levels will be affected by the oxygen depletion. If the oxygen level prior to intentional depletion is close to the threshold value, then the intentional depletion will reduce the dissolved oxygen below the threshold value described above, which will result in a sudden drop in enzyme electrode current. On a sliding scale, the earlier the drop in enzyme electrode occurs after applying the negative bias, the closer the oxygen concentration is to the threshold value. Alternatively, if no drop occurs within a predetermined time window, it can be concluded that the oxygen level is above the threshold value at the sensor location. In some cases, this intentional depletion method may be preferable because it provides information on whether the particular sensor is oxygen starved or not, rather than only measuring the oxygen concentration in the area of the sensor. In vivo oxygen measurements as described above can be valuable for many reasons, including indicating encapsulation of the sensor. For example, when the sensor is encapsulated, oxygen levels are low.

In other embodiments, the electrodes can have different bias potentials to measure different parameters. For example, the bias potential on a first working electrode can be turned off, or reduced to zero, and when the electrode is turned off, $H_2O_2$ will not be reduced. When the bias potential is later turned back on, the signal achieved can be indicative of $H_2O_2$ concentration and diffusion in the area of the sensor.

Measuring one or more parameters may be accomplished by processing signals associated with the sensor elements having alternating bias potential. Measuring one or more parameters can also be accomplished by processing signals associated with the sensor elements having alternating bias potential. In certain embodiments, the processor module may be programmed to measure parameters by comparing sensor data with certain data patterns known to correspond to the expected values. Upon detection of abnormal measured values, processing of the data streams associated with the one or more sensor elements may be adjusted. For example, in embodiments in which weighted averages or weighted sums are used to estimate analyte concentration value, sensor data associated with the sensor element showing normal parameter levels (or data from any collocated sensor) may be accorded more weight, and sensor data associated with the sensor element showing abnormal parameter values (or data from any collocated sensor) may be accorded less (or no) weight. In some embodiments, the processing module can process data from the one or more sensors measuring in vivo parameters to determine a response (such as, for example, any of the responses to sensor failure described herein).

In some embodiments, a dual-electrode or multi-electrode sensor can be configured and arranged to detect two analytes and/or configured as plenzyme and minenzyme electrodes. In certain embodiments of an analyte sensor, a first working electrode (such as, for example, an electroactive surface of a first elongated body) can be configured and arranged to generate a first signal containing an analyte component and a baseline, and a second working electrode (such as, for example, an electroactive surface of a second elongated body) can be configured and arranged to generate a second signal containing baseline without an analyte component. In one such system, the first electrode can function as a hydrogen peroxide sensor including a membrane system containing glucose-oxidase disposed thereon, which operates as described herein. The second electrode can be a hydrogen peroxide sensor configured similar to the first electrode, but with a modified membrane system (without active enzyme, for example). This second electrode can provide a signal composed mostly of the baseline signal. A processing module can process the data streams from the first and second electrode and identify a sensor failure and determine a response (such as, for example, any of the responses to sensor failure described herein).

In some embodiments, the sensor system includes a plurality of sensor elements, each with different enzyme domain properties. As described elsewhere herein, in certain embodiments, the sensor system includes a plurality of sensor elements each designed to have a different sensitivity or current sensitivity than the other sensor element(s). In one embodiment, the differences in sensor sensitivity or current density may be achieved by modifying each sensor element to have a different amount of enzyme. In other embodiments, one of the plurality of sensor elements may have an enzyme domain which contains polymers that contain mediators and enzymes that chemically attach to the polymers. The mediator used may oxidize at lower potentials than hydrogen peroxide, and thus fewer oxidizable interferents are oxidized at these low potentials. Accordingly, one of the sensor elements may have a very low baseline (namely, a baseline that approaches a zero baseline and that does not receive substantial signal contribution from non-glucose-related noise), such that the signal generated therefrom can be used to compare with the signal from another sensor element operating at a higher bias potential. By comparing the signals, the presence of interferents can be detected. Furthermore, in certain embodiments, the baseline present in the signal from the sensor element operating at a higher bias potential may be calculated (from the signal generated from the sensor element operating with a baseline of about zero) by comparing the signals from the two sensor elements (such as, for example, by subtracting one signal from another signal after accounting for scaling). In turn, signal contribution from non-glucose-related noise can be subtracted from the signal of the sensor element operating at a higher bias potential, thereby improving its signal's the signal to noise ratio, which results in greatly improved sensor accuracy. In certain embodiments, one of the plurality of sensor elements may have an enzyme domain which uses a mediator that may reduce or eliminate the need for oxygen, as the mediator take the place of oxygen in the enzyme reaction. Such a sensor element may be tuned for (and configured to detect) low oxygen environments, while other sensor elements are used in normal or high in vivo oxygen environments.

In certain embodiments, the first working electrode can be disposed beneath an enzymatic enzyme domain (or portion of the sensor membrane) including an active enzyme configured to detect the analyte or an analyte-related compound. Accordingly, the first working electrode can be configured to generate a first signal including both a signal related to the analyte and a signal related to non-analyte electroactive compounds (such as, for example, physiological baseline, interferents, and non-constant noise) that have an oxidation/reduction potential that overlaps with the oxidation/reduction potential of the analyte. The second working electrode can be disposed beneath an enzymatic enzyme domain (or portion of the sensor membrane) that includes a different form of the enzyme or a different enzyme. For example, in one embodiment, the second working electrode can be disposed beneath an enzymatic domain (or portion of the sensor membrane) including flavin adenine dinucleotide (FAD)-dependent glucose dehydrogenase. As another example, in one embodiment, the second working electrode can be disposed beneath an enzymatic domain (or portion of the sensor membrane) including a pyrroloquinoline (PQQ)-dependent glucose dehydrogenase. In some embodiments, the second working electrode can generate a second signal related to the analyte. In some embodiments, the second working electrode can generate a signal related to the analyte and a signal related to non-analyte electroactive compounds (such as, for example, physiological baseline, interferents, and non-constant noise) that have an oxidation/reduction potential that overlaps with the oxidation/reduction potential of the analyte. The noise of the sensor contains signal contribution due to non-analyte electroactive species (such as, for example, interferents) that have an oxidation/reduction potential that substantially overlaps the oxidation/reduction potential of the analyte. In some embodiments of a dual-electrode analyte sensor configured for fluid communication with a host's circulatory system, the non-analyte related electroactive species includes at least one species selected from the group including interfering species, non-reaction-related hydrogen peroxide, and other electroactive species.

In one embodiment, a system can have a first enzymatic electrode and a second non-enzymatic electrode, and a processing module may be used by comparing signals associated with the different electrodes. In certain embodiments, the processor module may be programmed to identify sensor failure or in vivo conditions by comparing sensor data with known data patterns or values. In some embodiments in which weighted averages or weighted sums are used to estimate analyte concentration value, sensor data associated with a first sensor element may be accorded more weight, and sensor data associated with a second sensor element may be accorded less (or no) weight. In some embodiments, the processing module can process data from the plurality of sensors having various different enzyme layers (or no enzyme layers) to identify a sensor failure or in vivo condition, and to determine a response (such as, for example, any of the responses to sensor failure described herein).

Figure 7:
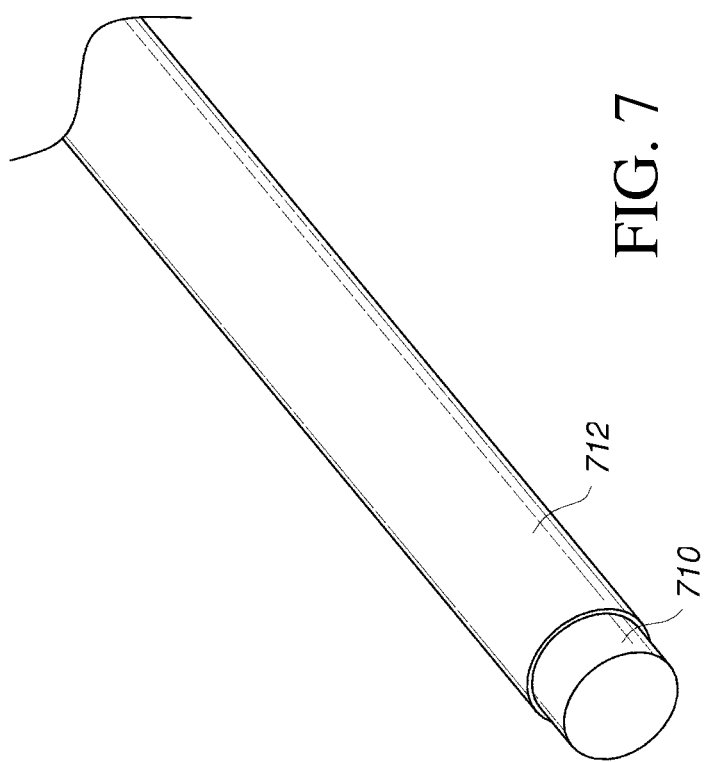
FIG. 7 is a view of one embodiment comprising a fiber optic core.

In another embodiment, a wire sensor can include a fiber optic core. As well as being the substrate on which the sensor can be built, the fiber optic core can be used as an additional sensor. In some preferred embodiments, a sensor can be formed onto the outer surface of a fiber optic core. FIG. 7 shows one embodiment of a sensor with a fiber optic core, wherein a sensor 712 is formed onto the outer surface of a fiber optic core 710. The fiber optic core 710 can be fabricated to be fatigue resistant and strong, as compared to a traditional polymer or metal core. In some embodiments, a polymer or other material can surround a bundle, array, or single fiber. The fiber optic core can be constructed using multiple fibers, bundles, arrays, or single fibers. In some embodiments, a bundle or array of fibers can contain one or more different sensors. In some embodiments, the sensor system can have an elongated core having a fiber optic sensor, and an electrochemical analyte sensor can be formed onto the outer surface of the elongated core.

Furthermore, the fiber optic sensors can be configured to detect a variety of analytes using known techniques. For example, light can be delivered at one frequency. After the light contacts the target analyte, the light can be absorbed and remitted at a different wavelength. The data can be collected and the light can be split into the different sensed wavelengths. One of skill in the art can appreciate that a wide variety of such optical techniques can be used for measuring analytes or other in vivo properties. Such optical techniques include optical absorption spectroscopy (such as, for example, pulse oximetry), polarimetry, Raman spectroscopy, FTIR, and optical coherence tomography.

In some embodiments, fiber optic sensors can also be useful for the detection of blood, various analytes such as glucose and oxygen, and various proteins, hormones, DNA, RNA, and the like. Fiber optic sensors can additionally be used to sense lactic acid to detect cell death. In certain embodiments, a fiber optic core can also be useful in optical imaging and electrical inputs, electrical outputs, electrical or electrochemical sensing, flow sensing, and pressure sensing. Embodiments with a fiber optic core can also be used for optical imaging during surgeries where the fiber optic can be used as a visual tool and the electrodes can be used to sense, stimulate or produce some other electrical action. Fiber optic sensors can also be used to position light energy.

Sensor systems having a fiber optic core can be used in a variety of ways. In some embodiments, the sensor and fiber optic core can be used to measure the same parameters (such as, for example, analyte concentration). In yet other embodiments, the sensor and fiber optic core can be used to measure different parameters. A processor can be configured to compare one or more parameters measured by the sensor to one or more parameters measured by the fiber optic core. In some embodiments, the processor can compare a magnitude of a parameter measured by a first sensor to the magnitude of a parameter measured by a fiber optic core. In other embodiments, the processor can be programmed to compare sensor data and fiber optic core data with expected known or in vitro values. In some embodiments, the processor can compare the magnitude of a parameter measured by a first sensor, and the magnitude of a parameter measured by a fiber optic core, to known or in vitro values. In certain embodiments, a failure can be identified when the magnitude of a parameter measured by a first sensor is different from the magnitude of a parameter measured by a fiber optic core by a predetermined amount. In certain embodiments, the processor module may be programmed to identify sensor failure by comparing sensor data with certain data patterns known to correspond to such failure. Upon detection of sensor failure, processing of the plurality of data streams associated with their respective plurality of sensor elements may be adjusted. For example, in embodiments in which weighted averages or weighted sums are used to estimate analyte concentration value, sensor data associated with the sensor element configured with the fiber optic core may be accorded more weight, and sensor data associated with the sensor element may be accorded less (or no) weight. In some embodiments, the processing module can process data from the fiber optic core and sensors to determine a response (such as, for example, any of the responses to sensor failure described herein).

In certain embodiments, both of the working electrodes of a dual-electrode analyte sensor can be disposed beneath one membrane system, with the following exceptions. The first working electrode can be disposed beneath an enzymatic enzyme domain (or portion of the sensor membrane) including an active enzyme configured to detect the analyte or an analyte-related compound. Accordingly, the first working electrode can be configured to generate a first signal including both a signal related to the analyte and a signal related to non-analyte electroactive compounds (such as, for example, physiological baseline, interferents, and non-constant noise) that have an oxidation/reduction potential that overlaps with the oxidation/reduction potential of the analyte. This oxidation/reduction potential may be referred to as a "first oxidation/reduction potential" herein. The second working electrode can be disposed beneath a non-enzymatic enzyme domain (or portion of the sensor membrane) that includes either an inactivated form of the enzyme contained in the enzymatic portion of the membrane or no enzyme. In some embodiments, the non-enzymatic portion can include a non-specific protein, such as BSA, ovalbumin, milk protein, certain polypeptides, and the like. The non-enzymatic portion generates a second signal associated with noise of the analyte sensor. The noise of the sensor contains signal contribution due to non-analyte electroactive species (such as, for example, interferents) that have an oxidation/reduction potential that substantially overlaps the first oxidation/reduction potential (that is, that overlap with the oxidation/reduction potential of the analyte). In some embodiments of a dual-electrode analyte sensor configured for fluid communication with a host's circulatory system, the non-analyte related electroactive species includes at least one species selected from the group including interfering species, non-reaction-related hydrogen peroxide, and other electroactive species.

In one embodiment, the dual-electrode analyte sensor can be a glucose sensor having a first working electrode and/or second working electrode configured to generate a first signal associated with both glucose and non-glucose related electroactive compounds that have a first oxidation/reduction potential. Non-glucose related electroactive compounds can be any compound, in the sensor's local environment that has an oxidation/reduction potential substantially overlapping with the oxidation/reduction potential of $H_2O_2$, for example. While not wishing to be bound by theory, it is believed that the glucose-measuring electrode can measure both the signal directly related to the reaction of glucose with GOx (produces $H_2O_2$ that is oxidized at the working electrode) and signals from unknown compounds that are in the blood surrounding the sensor. These unknown compounds can be constant or non-constant (such as, for example, intermittent or transient) in concentration and/or effect. In some circumstances, it is believed that some of these unknown compounds are related to the host's disease state. For example, it is known that blood chemistry changes dramatically during/after a heart attack (such as, for example, pH changes, concentration of various blood components/protein may change, and the like). Additionally, a variety of medicaments or infusion fluid components (such as, for example, acetaminophen, ascorbic acid, dopamine, ibuprofen, salicylic acid, tolbutamide, tetracycline, creatinine, uric acid, ephedrine, L-dopa, methyl dopa and tolazamide) that may be given to the host may have oxidation/reduction potentials that overlap with that of $H_2O_2$.

The non-analyte (e.g., non-glucose) signal produced by compounds other than the analyte (such as, for example, glucose) may obscure the signal related to the analyte, may contribute to sensor inaccuracy, and is considered background noise. Background noise includes both constant and non-constant components and is to be removed to accurately calculate the analyte concentration. While not wishing to be bound by theory, it is believed that the sensor of some of the embodiments are designed (e.g., with symmetry, coaxial design and/or integral formation, and interference domain of the membrane described elsewhere herein) such that the first and second electrodes are manufactured with substantially the same specifications, which enables substantially equivalent measurement of various in vivo properties.

Identification of Sensor Failures

Various ways in which sensor failures can be identified are discussed above. Any measured parameters described herein, and additional information (such as, for example, time of day, time after implant, temperature information or decay waveforms, etc.) can be considered and compared to identify sensor failure. Any measured parameters described herein, and additional information (such as, for example, time of day, time after implant, temperature information or decay waveforms, etc.) can also be considered and compared to provide information on reliability of sensor system values.

Additionally, in some embodiments, comparison and analysis can be performed on signals from sensors made to have different properties. The comparison and analysis can include integrating or averaging signals from a plurality of sensor elements. In some embodiments having one or more sensors with have different sensitivities, the sensor electronics may be configured to accord less (or no) weight to a high sensitivity sensor element, as compared to a low sensitivity sensor element, in environments associated with low oxygen and high glucose concentration, for example. Conversely, the sensor electronics may be configured to accord more weight to the high sensitivity sensor element in environments associated with high oxygen and low glucose concentration, for example. As an alternative to weighting, the sensor electronics may be configured to poll sensor data from the low glucose sensitivity sensor only when an environment associated with a low oxygen environment is detected.

In some embodiments, a system can have a first sensor can have a first characteristic (such as, a first sensitivity, a first membrane layer, a first interferent layer, a first programmed time period range, a first bias potential, be configured to measure a constant analyte or oxygen, a first enzymatic layer, or be a fiber optic core), and a second sensor can have a second characteristic (such as, a second sensitivity, a second membrane layer, a second interferent layer, a second programmed time period range, a second bias potential, be configured to measure a second constant analyte or oxygen, a second enzymatic layer, or be a sensor adjacent to a fiber optic core), and the signals from the two differently manufactured sensor elements can be compared and analyzed by a processing module to provide information not only about glucose concentration, but information about other parameters that can affect sensor performance or lead to sensor failure. Additionally, the system can be configured to respond to the measured parameters or to the identified change in sensor performance or to the identified sensor failure.

By comparing data from the two or more sensors having different characteristics, various sensor failures can be identified. Any reduction in accuracy or reliability can be considered sensor failure. Sensor failure can be a temporary failure, or a long-term or permanent failure. Sensor failure can occur due to many conditions or events, such as, for example, moisture ingress, membrane damage, encapsulation and end of life of the sensor, dip and recover failures, and biomaterial buildup or biofouling. Moisture ingress and membrane damage are sensor failures that often occur within the sensor system itself, and can arise due to a variety of reasons. Failure of transcutaneous and implantable sensors is generally more often due to in vivo properties and physiological responses in surrounding tissues. For example, a reduction in sensor accuracy following implantation of the sensor is one common sensor failure phenomenon commonly observed. This phenomenon is sometimes referred to as a "dip and recover" process. Dip and recover is believed to be triggered by trauma from insertion of the implantable sensor, and possibly from irritation of the nerve bundle near the implantation area, resulting in the nerve bundle reducing blood flow to the implantation area. Alternatively, dip and recover may be related to damage to nearby blood vessels, resulting in a vasospastic event. Any local cessation of blood flow in the implantation area for a period of time leads to a reduced amount of glucose in the area of the sensor. During this time, the sensor has a reduced sensitivity and is unable to accurately track glucose. Thus, dip and recover manifests as a suppressed glucose signal. The suppressed signal from dip and recover often appears within the first day after implantation of the signal, most commonly within the first 12 hours after implantation. Importantly, dip and recover normally resolves within 6-8 hours. Identification of dip and recover can provide information to a patient, physician, or other user that the sensor is only temporarily affected (or that there is only a temporary sensor failure) by a short-term physiological response, and that there is no need to remove the implant as normal function will likely return within hours.

Another example of sensor failure due to in vivo properties and physiological responses in surrounding tissues arises when the implantable sensor becomes coated in biological material. During wound healing and foreign body response, the surface of the implantable sensor can become coated in protein or other biological material to such an extent that the sensor is unable to accurately track blood glucose. This sensor failure phenomenon is sometimes called "biofouling," and biofouling often manifests itself as a downward shift in sensor sensitivity over time. Similarly, the implantable sensor can become encapsulated by biological material to such an extent that the sensor is unable to provide glucose data, and the sensor is considered to effectively be at end of life. In some cases, the implantable device can be programmed to correct for errors associated with biofouling and end of life, so that identification of these phenomenon aids in providing more accurate glucose data. Identification of these phenomena also generally indicates that the device has failed and should be replaced.

Sensor electronics can be used to consider and compare data from the two or more sensors. In some embodiments, such sensor electronics can further be used to determine a quality score. In some embodiments, the sensor electronics can be used to determine and identify the type of sensor failure present. The sensor electronics may include a potentiostat, A/D converter, RAM, ROM, transceiver, processor, and/or the like. The potentiostat may be used to provide a bias to the electrodes and to convert the raw data (e.g., raw counts) collected from a sensor to an analyte concentration value (such as, for example, a glucose concentration value expressed in units of mg/dL). The transmitter may be used to transmit a first and second signal (or additional signals) to a receiver, where additional data analysis and/or calibration of analyte concentration can be processed. In certain embodiments, the sensor electronics may perform additional operations, such as, for example, data filtering and noise analysis.

In some embodiments, a processor can be programmed to compare sensor data from multiple sensors. In some embodiments, the processor can compare a magnitude of a parameter measured by a first sensor to the magnitude of a parameter measured by a second sensor. In other embodiments, the processor can be programmed to compare sensor data with expected known or in vitro values. In some embodiments, the processor can compare the magnitude of a parameter measured by a first sensor, and the magnitude of a parameter measured by a second sensor, to known or in vitro values. In certain embodiments, a failure can be identified when the magnitude of a parameter measured by a first electrode is different from the magnitude of a parameter measured by a second electrode by a predetermined amount.

In some embodiments, the processor can identify one data input, or alternatively can identify one or more of the measured parameters described herein. For example, the processor can be programmed to compare the sensitivity of each sensor a certain time or times after implantation. As another example, the processor can compare baseline changes between each sensor and known in vitro baseline values. In yet another example, the processor can be programmed to compare amplitude and sensitivity changes between two or more sensors. In yet another exemplary embodiment, the processor can compare baseline changes between each sensor and a known in vitro value. In some embodiments where multiple measurements are considered, the processor can be programmed to give each measurement an appropriate weight. For example, where it is known that small changes in amplitude (such as, for example, deviations of less than about 5%) correspond with a high probability (such as, for example, 90% or more) of failure, but small changes in baseline (such as, for example, deviations of less than about 5%) correspond with a lower probability (such as, for example, 50% or more) of failure, the processor can be programmed to compare the amplitudes and changes in baseline in a weighted manner. The processor can also be programmed to recognize that one or more deviations over a certain threshold (such as, for example, deviations of 1%, 2%, 5%, or 10% or more) between each sensor's measurements of various parameters may be indicative of failure. For example, if one, two, three, or more differences (such as, for example, amplitude and changes in sensitivity both vary by over 5%) are detected, then one or more of the sensors can be considered failed, in some embodiments.

Response to Sensor Failure

Once a sensor failure is detected and identified, the sensor system can be programmed to respond in any one of a variety of ways. In some embodiments, the sensor system can provide a quality score, which provides information on sensor reliability, accuracy, and sensor failure. In some embodiments, the quality score can be a numerical value. Although various scales can be used for the quality score, in one embodiment, a score of 100 can indicate perfect tracking for all measured parameters.

Some embodiments can include a closed loop analyte sensor system, wherein the system uses one or more sensors to measure in vivo parameters and calculate analyte values, and wherein the system can deliver an appropriate amount of a fluid to the patient (such as, for example, through a pump). Such closed loop systems can monitor and control analyte values in a host. In some embodiments, the analyte measured is glucose, and the fluid delivered is insulin. In some embodiments of a closed loop system, a quality score can be considered by the system in determining a response. In some embodiments, of a closed loop system, a quality score can be considered by the system to control the analyte to a target value. In other embodiments of a closed loop system, a quality score can be considered by the system to control the analyte to a target range of values. For example, if the quality score is high, a closed loop system can respond by controlling the analyte (such as, for example, glucose) to a target value (such as, for example, 72 mg/dL), in some embodiments. In other embodiments, the system can respond by controlling the analyte (such as, for example, glucose) to a narrow target range (such as, for example, from about 70 mg/dL to about 100 mg/dL). A high quality score value is a relative term and depends on the scale used; however, in one embodiment where 100 indicates perfect tracking, a high quality score may be any score above 60, 65, 75, 80, 85, 90, or 95.

In some embodiments, for example, if the quality score is at a medium level, the closed loop system can respond by controlling the analyte (such as, for example, glucose) to a broad target range (such as, for example, from about 70 mg/dL to about 1030 mg/dL), in some embodiments. A medium quality score value is a relative term and depends on the scale used; however, in one embodiment where 100 indicates a perfect tracking, a medium quality score may be any score between about 20-95, 35-85, 45-75, 55-65, or about 50 or about 60.

In certain embodiments, if the quality score is low, the closed loop system can respond by controlling the analyte (such as, for example, glucose) to a broad target range (such as, for example, from about 65 mg/dL to about 150 mg/dL). In some embodiments, the system can respond by instructing or notifying the user to use alternative methods (such as, for example, fingerstick glucose monitoring method) to monitor analyte levels. The system can also respond by temporarily or permanently suspending the closed loop system, such as, for example. The system can also respond to a low quality score in other various ways, as further described below with respect to sensor failure. A low value is a relative term and depends on the scale used; however, in one embodiment where 100 indicates a perfect tracking, a low quality score may be any score below 5, 10, 15, 20, 25, 30, 35, 40, 45, or 50, in some embodiments.

While the above examples discuss closed loop analyte sensor systems, quality score data can be utilized as part of a semi-closed loop system and by any analyte sensor systems. For example, a semi-closed loop system can operate by suspending fluid delivery when analyte levels are at a certain level or within a certain range of values. In some semi-closed loop systems, the fluid delivered is insulin and the analyte measured is glucose. In some embodiments of a semi-closed loop system, a quality score can be considered by the system in determining a response. In some embodiments, of a semi-closed loop system, a quality score can be considered by the system to control the analyte to a target value. In other embodiments of a closed loop system, a quality score can be considered by the system to control the analyte to a target range of values. In some semi-closed loop systems, the quality score can be considered by the system to suspend delivery of a fluid until measured analyte values are within a certain target range. Quality score data can also be utilized by other analyte sensors, such as, for example, sensors that measure analyte values and/or provide data to a user. In some embodiments, quality score data can be considered by an analyte sensor in determining an appropriate response. For example, in some embodiments, a low quality score (as defined above), can prompt a system to notify or instruct a user to use an alternative analyte sensing method due to sensor failure. In other embodiments, the quality score can be provided to a user to inform the user as to the reliability of sensor data.

The quality score can be calculated in any of a variety of ways. In one embodiment, a parameter measured by a first sensor is compared to a parameter measured by a second sensor parameter. In one embodiment, multiple parameters measured by the first sensor are compared to multiple parameters measured by the second sensor. In certain embodiments, one or more measured of the measured parameters are weighted in calculating the quality score. For example, the magnitude between the two or more sensor's amplitude, sensitivity, change in sensitivity, baseline, change in baseline, or various scaled raw signals can be considered. In some embodiments, an algorithm may be applied to the sensor data to calculate the quality score.

Once calculated, the quality score can be provided to the user or can be used by the system to develop an appropriate response, as described above. In addition to aiding in monitoring and controlling or partially controlling fluid delivery in closed loop or semi-closed loop systems, the quality score can be utilized to determine or select any of a variety of appropriate responses. For example, in some embodiments, the system can automatically shut off the sensor, either temporarily or permanently. Additionally, the system can provide an audible or visual alarm. In some embodiments, the system can provide various audible or visual information, such as a numerical quality score indicator to inform the user as the reliability of the analyte measurements. In some embodiments, the system can provide instructions to the user, such as directing the user to wait an appropriate amount of time or directing the user to change sensors. In some embodiments, the system can provide instruct the user to use an alternative method to measure analyte values (such as, for example, a fingerstick glucose monitoring method). In other embodiments, the system can respond by re-calibrating or compensating in some way.

In addition to calculating or providing a quality score, in some embodiments, a sensor system can identify a particular type of sensor failure, such as dip and recover, biofouling, or end of life, as described above. When a particular type of sensor failure is identified, the system can respond in a particular way. For example, if dip and recover conditions are identified, the system can notify a user to use another method to monitor blood glucose levels temporarily until the sensor regains full function. For example, the sensor system can notify the user that sensor data are temporarily affected by implantation of the device, and that glucose should be monitored by another method in the interim. In another embodiment, the system can provide information describing the patient's physiological condition. In one embodiment, the system can explain the cause of the interruption in sensor function. In one embodiment, the sensor system can display an estimated time at which the sensor may likely function properly again. In one embodiment, the sensor system can completely cease display of data. In another embodiment, the system can provide a message, sound an alarm, or otherwise notify the user when the dip and recover event has resolved and that the sensor is functioning properly again. In some embodiments, the sensor system can notify or inform the user through a visually displayed message on a user interface, and in other embodiments, the system can notify or inform the user through audible alarms or messages. In some embodiments, the sensor system can notify or inform the user through a combination of both visual and audible alarms or messages.

After certain sensor failures are identified, such as biofouling or encapsulation, the sensor may no longer be reliable, providing inaccurate sensor data. To prevent further use of the unreliable sensor, some embodiments notify a user to change the sensor after it has been determined that the sensor should no longer be used. Once it is determined that the sensor should no longer be used, the sensor system can notify a user that a new sensor should be implanted by audibly and/or visually prompting a user to use a new sensor and/or shutting down a display or ceasing to display sensor data on the display, for example. The alarm can also inform the user why sensor reuse may be undesirable, such as potentially providing inaccurate and unreliable sensor readings. Identification of biofouling or end of life can alternatively or additionally cause the sensor system to fully or partially shut down and/or cease display of sensor data on a user interface of the sensor system. Continuing to use the sensor once biofouling or encapsulation resulting in end of life is detected, can be dangerous to the user because the sensor may provide inaccurate data upon which the user may rely. In some embodiments, the implantable device can also be programmed to correct for errors associated with biofouling and end of life, so that identification of these sensor failures also aids in providing more accurate glucose data.

In some embodiments, a receiver, which can also be referred to as a display device or user interface, can be in communication (e.g., wired or wireless) with an electronics module, which can be within the sensor housing. The receiver can be an application-specific hand-held device, or a general purpose device, such as a P.C., smart phone, tablet computer, and the like. In one embodiment, a receiver can be in data communication with the sensor housing for receiving sensor data, such as raw and/or displayable data, and include a processing module for processing and/or display the received sensor data. The receiver can also and include an input module configured to receive input, such as calibration codes, reference analyte values, and any other information discussed herein, from a user via a keyboard or touch-sensitive display screen, for example, and can also be configured to receive information from external devices, such as insulin pumps and reference meters, via wired or wireless data communication. The input can be processed alone or in combination with information received from the sensor electronics module. The receiver can be programmed to notify or inform the user in the various ways described above, such as, for example displaying messages or visual information, providing audible instructions, and/or sounding alarms.

Example 1

Two Sensors Having Different Interference Layers

Dual-electrode sensors (having a configuration similar to the embodiment shown in FIG. 1) can be constructed from two platinum wires. The first electrode had a first interference domain formed from a cellulosic derivative, and of a thickness of about 0.5 microns to block the flux of interferents. The second electrode was formed without an interference layer.

An experiment was conducted whereby various fluid samples were applied to the electrodes, and the signals from the two electrodes were compared. A processing module was used to detect elevated levels of interferents by comparing the signals from each sensor. Upon identification of high interferent levels, the processing module identified a sensor failure. Based on programmed settings, the processing module in communication with a receiver, provided information related to the sensor failure as expected.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; U.S. Pat. Nos. 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No.

2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; and U.S. application Ser. No. 13/784,523 filed on Mar. 4, 2013 and entitled "ANALYTE SENSOR WITH INCREASED REFERENCE CAPACITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for detecting a sensor failure in a continuous analyte monitoring system implanted in a host, the method comprising:
    applying a first bias potential to a first electrode implanted in the host;
    receiving first sensor data from the first electrode, wherein the first sensor data are indicative of a property corresponding to the first electrode;
    applying a second bias potential to a second electrode implanted in the host, wherein the first bias potential and the second bias potential are different;

receiving second sensor data from the second electrode, wherein the second sensor data are indicative of the property corresponding to the second electrode;

comparing, using a processor module, the property corresponding to the first electrode with the property corresponding to the second electrode; and identifying a failure in at least one of the first electrode or the second electrode when a property magnitude of the first electrode is different from a property magnitude of the second electrode by a predetermined value.

2. The method of claim 1, wherein the property is sensor sensitivity to an analyte.

3. The method of claim 2, wherein the property is baseline.

4. The method of claim 1, wherein the first electrode and the second electrode are separated by a distance of less than 1 mm at a closest proximity.

5. The method of claim 1, wherein the first electrode and the second electrode are separated by a distance of less than 0.5 mm at a closest proximity.

6. A method for detecting a sensor failure in a continuous analyte monitoring system implanted in a host, the method comprising:

applying a first bias potential to a first electrode implanted in the host;

receiving first sensor data over a time period from the first electrode, wherein the first sensor data are indicative of a property corresponding to the first electrode, wherein the property is at least one of sensor sensitivity or baseline;

applying a second bias potential to a second electrode implanted in the host, wherein the first bias potential and the second bias potential are different;

receiving second sensor data over the time period from the second electrode, wherein the second sensor data are indicative of the property corresponding to the second electrode;

determining, using a processor module, over the time period a correlation between the property corresponding to the first electrode with the property corresponding to the second electrode; and identifying a failure in at least one of the first electrode or the second electrode when the correlation is less than a predetermined value.

7. A method for detecting a sensor failure in a continuous analyte monitoring system implanted in a host, the method comprising:

applying a potential to a continuous analyte sensor implanted in the host;

receiving sensor data over a time period from the continuous analyte sensor, the sensor data comprising at least one sensor data point, wherein the applying of the potential is at least in part during the time period;

processing the at least one sensor data point to determine a first value associated with a first analyte concentration value, the first value determined using a first calculation;

processing the at least one sensor data point to determine a second value associated with a second analyte concentration value, the second value determined using a second calculation different from the first calculation;

comparing, using a processor module, the first value to the second value;

identifying a sensor failure if a difference between the first value and the second value exceeds a predetermined amount; and responsive to identifying the sensor failure, triggering an alert indicating the sensor failure.

8. The method of claim 7, wherein the alert indicates that the sensor failure is temporary.

9. The method of claim 7, wherein the alert comprises a prompt to the host to implant a replacement continuous analyte sensor.

10. The method of claim 7, further comprising preventing display of analyte concentration values from the continuous analyte sensor.

11. The method of claim 7, further comprising, responsive to identifying the sensor failure, shutting off the continuous analyte sensor.

12. The method of claim 7, wherein the alert comprises at least one of an audible alert, a tactile alert, or a visible alert.

13. The method of claim 7, wherein the first calculation is based at least in part on the Michaelis-Menten equation and the second calculation is based at least in part on a linear regression.

14. The method of claim 7, further comprising determining a quality score based at least in part on the comparing of the first value to the second value, wherein the identifying of the sensor failure is based at least in part on the quality score.

15. The method of claim 14, further comprising displaying the quality score to the host.

16. The method of claim 7, further comprising, responsive to identifying the sensor failure, prompting the host to provide a reference analyte concentration value.

17. The method of claim 7, wherein the identifying the sensor failure is also based at least in part on a time of day.

18. The method of claim 7, wherein the identifying the sensor failure is also based at least in part on a time after the continuous analyte sensor was implanted in the host.

19. The method of claim 7, further comprising heating tissue of the host with a heating element of the continuous analyte sensor, wherein the identifying the sensor failure is based at least in part on a property of the heating element.

20. The method of claim 7, further comprising, responsive to identifying the sensor failure, switching operation of the continuous analyte sensor from a first mode to a second mode.

* * * * *

UNITED STATES PATENT AND TRADEMARK OFFICE
CERTIFICATE OF CORRECTION

PATENT NO. : 10,881,339 B2  
APPLICATION NO. : 13/789279  
DATED : January 5, 2021  
INVENTOR(S) : Thomas A. Peyser et al.

Page 1 of 1

It is certified that error appears in the above-identified patent and that said Letters Patent is hereby corrected as shown below:

In the Specification

In Column 4, Line 67, delete "andrenostenedione;" and insert --androstenedione;--.

In Column 5, Line 15, delete "diptheria" and insert --diphtheria--.

In Column 5, Line 20, delete "g alacto se-1-pho sphate" and insert --galactose-1-phosphate--.

In Column 5, Line 22, delete "perioxidase;" and insert --peroxidase;--.

In Column 5, Line 31, delete "sissomicin;" and insert --sisomicin;--.

In Column 5, Line 35, delete "duodenalisa," and insert --duodenalis,--.

In Column 5, Line 43, delete "Trepenoma pallidium," and insert --Treponema pallidum,--.

In Column 5, Line 44, delete "stomatis" and insert --stomatitis--.

In Column 5, Lines 64-65, delete "(barbituates," and insert --(barbiturates,--.

In Column 6, Line 11, delete "(3MT)," and insert --(3-MT),--.

In Column 6, Line 13, delete "(5HT)," and insert --(5-HT),--.

In Column 6, Line 13, delete "(FHIAA)." and insert --(5-HIAA).--.

In Column 14, Line 16, delete "polyethyleneterephthalate," and insert --polyethylene terephthalate,--.

In Column 43, Line 64, delete "electrode" and insert --electrode.--.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*